US007960362B2

(12) United States Patent
Kandimalla et al.

(10) Patent No.: US 7,960,362 B2
(45) Date of Patent: Jun. 14, 2011

(54) SYNTHETIC AGONISTS OF TLR9

(75) Inventors: Ekambar Kandimalla, Southboro, MA (US); Mallikarjuna Putta, Burlington, MA (US); Daqing Wang, Bedford, MA (US); Dong Yu, Westboro, MA (US); Lakshmi Bhagat, Framingham, MA (US); Sudhir Agrawal, Shrewsbury, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/183,439

(22) Filed: Jul. 31, 2008

(65) Prior Publication Data
US 2009/0053206 A1     Feb. 26, 2009

Related U.S. Application Data

(60) Provisional application No. 61/015,292, filed on Dec. 20, 2007, provisional application No. 60/987,151, filed on Nov. 12, 2007, provisional application No. 60/983,601, filed on Oct. 30, 2007, provisional application No. 60/953,251, filed on Aug. 1, 2007.

(51) Int. Cl.
*A01N 43/04* (2006.01)
*A61K 39/00* (2006.01)
*A61K 45/00* (2006.01)
*C07H 21/02* (2006.01)

(52) U.S. Cl. .............. 514/44; 424/184.1; 424/278.1; 514/1.1; 536/23.1

(58) Field of Classification Search .............. 435/91.1, 435/375, 455, 184.1, 278.1; 514/44, 1.1; 536/23.1
See application file for complete search history.

(56) References Cited

U.S. PATENT DOCUMENTS

| 6,503,734 | B1 * | 1/2003 | Craft et al. ............ 435/69.1 |
| 6,790,640 | B2 * | 9/2004 | Craft et al. ............ 435/69.1 |
| 7,276,489 | B2 | 10/2007 | Agrawal et al. |
| 2006/0058254 | A1 | 3/2006 | Dina et al. |
| 2008/0292648 | A1 * | 11/2008 | Kandimalla et al. ....... 424/184.1 |
| 2008/0311112 | A1 * | 12/2008 | Hackam et al. ............ 424/130.1 |
| 2009/0317480 | A1 * | 12/2009 | Fearon et al. ............. 424/501 |

FOREIGN PATENT DOCUMENTS

| WO | WO 02/052002 | * | 7/2002 |
| WO | WO 2004/058179 | * | 7/2004 |

OTHER PUBLICATIONS

Zhao et al.; "Effect of Different Chemically Modified Oligodeoxynucleotides on Immune Stimulation"; Biochem. Pharmacol. 1996, 26:173-182.
Hemmi et al.; "A Toll-like receptor recognizes bacterial DNA"; Nature 2000, 408:740-745.
Zhao et al.; "Modulation of Oligonucleotide-Induced Immune Stimulation by Cyclodextrin Analogs"; Biochem Pharmacol. 1996, 52:1537-1544.
Zhao et al.; "Pattern and Kinetics of Cytokine Production Following Administration of Phosphorothioate Oligonucleotides in Mice"; Antisense Nucleic Acid Drug Dev. 1997, 7:495-502.
Zhao et al.; "Site of Chemical Modifications on CpG Containing Phosphorothioate Oligodeoxynucleotide Modulates its Immunostimulatory Activity"; Bioorg. Med. Chem. Lett. 1999, 9:3453-3458.
Zhao et al.; "Immunostimulatory Activity of CpG Containing Phosphorothioate Oligodeoxynucleotide is Modulated by Modification of a Single Deoxynucleoside"; Bioorg. Med. Chem. Lett. 2000, 10:1051-1054.
Yu et al.; "Accessible 5'-End of CpG-Containing Phosphorothioate Oligodeoxynucleotides is Essential for Immunostimulatory Activity"; Bioorg. Med. Chem. Lett. 2000, 10:2585-2588.
Yu et al.; "Modulation of Immunostimulatory Activity of CpG Oligonucleotides by Site-Specific Deletion of Nucleobases"; Bioorg. Med. Chem. Lett. 2001, 11:2263-2267.
Kandimalla et al.; "Effect of Chemical Modifications of Cytosine and Guanine in a CpG-Motif of Oligonucleotides: Structure-Immunostimulatory Activity Relationships"; Bioorg. Med. Chem. 2001, 9:807-813.
Kandimalla et al.; "Immunomodulatory Oligonucleotides Containing a Cytosine-Phosphate-2'-deoxy-7-deazaguanosine Motif as Potent Toll-Like Receptor 9 Agonists"; Proc Natl. Acad. Sci. USA, 2005, 102:6925-6930.
Kandimalla et al.; "A dinucleotide motif in oligonucleotides shows potent immunomodulatory activity and overrides species-specific recognition observed with CpG motif"; Proc Natl Acad. Sci USA, 2003, 100:14303-14308.
Cong et al.; "Self-stabilized CpG DNAs optimally activate human B cells and plasmacytoid dendritic cells"; Biochem Biophys Res Commun. 2003, 310:1133-1139.
Kandimalla et al.; "Secondary Structures in CpG Oligonucleotides Affect Immunostimulatory Activity"; Biochem Biophys Res Commun. 2003, 306:948-953.
Kandimalla et al.; "Divergent Synthetic Nucloetide Motif Recognition Pattern: Design and Development of Potent Immunomodulatory Oligodeoxyribonucleotide Agents with Distinct Cytokine Induction Profiles"; Nucleic Acids Res. 2003, 31:2393-2400.
Yu et al.; "Requirement of Nucleobase Proximal to CpG Dinucleotide for Immunostimulatory Activity of Synthetic CpG DNA"; Bioorg. Med. Chem. 2003, 11:459-464.
Bhagat et al.; "CpG Penta- and Hexadeoxyribonucleotides as Potent Immunomodulatory Agents"; Biochem Biophys Res Commun. 2003, 300:853-861. Yu et al.; "Immunomers'-Novel 3'-3'-Linked CpG Oligodeoxyribonucleotides as Potent Immunomodulatory Agents"; Nucleic Acids Res. 2002, 30:4460-4469.
Yu et al.; "Design, Synthesis, and Immunostimulatory Properties of CpG DNAs Containing Alkyl-Linker Substitutions: Role of Nucleosides in the Flanking Sequences"; J. Med. Chem. 2002, 45:4540-4548.
Yu et al.; "Potent CpG Oligonucleotides Containing Phosphodiester Linkages: In Vitro and In Vivo Immunostimulatory Properties"; Biochem Biophys Res. Commun. 2002, 297:83-90.

(Continued)

*Primary Examiner* — Jane Zara
(74) *Attorney, Agent, or Firm* — McDonnell Boehnen Hulbert & Berghoff LLP

(57) ABSTRACT

The invention relates to synthetic chemical compositions that are useful for modulation of Toll-Like Receptor (TLR)-mediated immune responses. In particular, the invention relates to agonists of Toll-Like Receptor 9 (TLR9) that generate unique cytokine and chemokine profiles.

6 Claims, 35 Drawing Sheets

OTHER PUBLICATIONS

Kandimalla et al.; "Conjugation of Ligand at the 5'-End of CpG DNA Affects Immunostimulatory Activity"; Bioconjug. Chem. 2002, 13:966-974.

Yu et al.; "Immunostimulatory Properties of Phosphorothioate CpG DNA Containing Both 3'-5'-and 2'-5-Internucleotide Linkages"; Nucleic Acids Res. 2002, 30:1613-1619.

Yu et al.; "Immunostimulatory Activity of CpG Oligonucleotides Containing Non-Ionic Methylphosphonate Linkages"; Bioorg. Med. Chem. 2001, 9:2803-2808.

Putta et al.; "Novel Oligodeoxynucleotide Agonists of TLR9 Containing N3-Me-dC or N1-Me-dG Modifications"; Nucleic Acids Res. 2006, 34:3231-3238.

Hornung et al.; "Quantitative Expression of Toll-Like Receptor 1-10 mRNA in Cellular Subsets of Human Peripheral Blood Mononuclear Cells and Sensitivity to CpG Oligodeoxynucleotides"; J. Immunol., 2002, 168:4531-4537.

Poltorak et al.; "Defective LPS Signaling in C3H/HeJ and C57BL/10ScCr Mice: Mutations in Tlr4 Gene"; Science, 1998, 282:2085-2088.

Underhill et al.; "The Toll-Like Receptor 2 is Recruited to Macrophage Phagosomes and Discriminates Between Pathogens"; Nature, 1999, 401:811-815.

Hayashi et al.; "The Innate Immune Response to Bacterial Flagellin Is Mediated by Toll-Like Receptor 5"; Nature, 2001, 410:1099-1103.

Zhang et al.; "A Toll-like Receptor That Prevents Infection by Uropathogenic Bacteria"; Science, 2004, 303:1522-1526.

Meier et al.; "Toll-Like Receptor (TLR) 2 and TLR4 Are Essential for Aspergillus-Induced Activation of Murine Macrophages"; Cell. Microbiol. 2003, 5:561-570.

Campos et al.; "Activation of Toll-Like Receptor-2 by Glycosylphosphatidylinositol Anchors from a Protozoan Parasite1"; J. Immunol, 2001, 167:416-423.

Hoebe et al.; "Identification of Lps2 as a Key Transducer of MyD88-Independent TIR Signalling"; Nature, 2003, 424:743-748.

Lund et al.; "Toll-like Receptor 9—mediated Recognition of Herpes Simplex Virus-2 by Plasmacytoid Dendritic Cells"; J. Exp. Med., 2003, 198:513-520.

Heil et al.; "Species-Specific Recognition of Single-Stranded RNA via Toll-like Receptor 7 and 8"; Science, 2004, 303:1526-1529.

Diebold et al.; "Innate Antiviral Responses by Means of TLR7-Mediated Recognition of Single-Stranded RNA"; Science, 2004, 303:1529-1531.

Hornung et al.; "Replication-Dependent Potent IFN-alpha Induction in Human Plasmacytoid Dendritic Cells by a Single-Stranded RNA Virus1"; J. Immunol., 2004, 173:5935-5943.

Akira et al.; "Toll-Like Receptors: Critical Proteins Linking Innate and Acquired Immunity"; Nature Immunol., 2001, 2:675-680.

Medzhitov; "Toll-Like Receptors and Innate Immunity"; Nature Rev. Immunol., 2001, 1:135-145.

Smith and Wickstrom; "Antisense c-myc and Immunostimulatory Oligonucleotide Inhibition of Tumorigenesis in a Murine B-Cell Lymphoma Transplant Model"; J. Natl. Cancer Inst., 1998, 90:1146-1154.

Vincenzo et al; "Novel Toll-Like Receptor 9 Agonist Induces Epidermal Growth Factor Receptor (EGFR) Inhibition and Synergistic Antitumor Activity with EGFR Inhibitors"; Clin. Cancer Res., 2006, 12(2):577-583.

* cited by examiner

Activity of agonists of TLR9 in HEK293 cells expressing mTLR9

Activity of agonists of TLR9 in HEK293 cells expressing mTLR9

Activity of agonists of TLR9 in HEK293 cells expressing mTLR9

Activity of agonists of TLR9 in HEK293 cells expressing mTLR9

Activity of agonists of TLR9 in HEK293 cells expressing mTLR9

Activity of agonists of TLR9 in HEK293 cells expressing mTLR9

Activity of agonists of TLR9 in HEK293 cells expressing mTLR9

Cytokine/chemokine profiles induced in human PBMC cultures

Cytokine/chemokine profiles induced in human PBMC cultures

Cytokine/chemokine profiles induced in human PBMC cultures

Figure 4I.

Cytokine/chemokine profiles induced in human PBMC cultures

| Compound No. | IFN-α (pg/ml) | IFN-α (pg/ml) |
|---|---|---|
| | 10 μg/ml | 1 μg/ml |
| 22 | | |
| 23 | | 2270.9 |
| 24 | | 1639.9 |
| 25 | 1344.8 | |
| 26 | 109.2 | |
| 27 | 0 | |
| 28 | 904.0 | |
| Media | 29.9 / 0 | 25.7 |

Figure 4J.

Cytokine/chemokine profiles induced in human PBMC cultures

| Compound No. | IL-6 (pg/ml) | IL-6 (pg/ml) |
|---|---|---|
| | 10 µg/ml | 1 µg/ml |
| 22 | 456.1 | |
| 23 | | 3115.2 |
| 24 | | 2936.1 |
| 25 | 591.2 | |
| 26 | 228.3 | |
| 27 | 67.8 | |
| 28 | 112.2 | |
| Media | 13.4 / 4.97 | 4.76 |

Figure 4K.

Cytokine/chemokine profiles induced in human PBMC cultures

| Compound No. | IL-12(pg/ml) | IL-12 (pg/ml) |
|---|---|---|
| | 10 µg/ml | 1 µg/ml |
| 22 | 94.25 | |
| 23 | | 795.3 |
| 24 | | 559.0 |
| 25 | 41.96 | |
| 26 | 95.11 | |
| 27 | 23.39 | |
| 28 | 36.43 | |
| Media | 9.2 / 9.36 | 52.2 |

Figure 4L.

Cytokine/chemokine profiles induced in human PBMC cultures

| Compound No. | iP-10 (pg/ml) | iP-10 (pg/ml) |
|---|---|---|
| | 10 μg/ml | 1 μg/ml |
| 22 | 661.7 | |
| 23 | | 2998.3 |
| 24 | | 1790.5 |
| 25 | 1247.7 | |
| 26 | 642.7 | |
| 27 | 139.7 | |
| 28 | 3650.6 | |
| Media | 8.0 / 29.3 | 22.7 |

Figure 4M.

Cytokine/chemokine profiles induced in human PBMC cultures

| Compound No. | MIP-α(pg/ml) | MIP-α(pg/ml) |
|---|---|---|
| | 10 µg/ml | 1 µg/ml |
| 22 | 92.65 | |
| 23 | | 458.4 |
| 24 | | 477.0 |
| 25 | 281.3 | |
| 26 | 218.3 | |
| 27 | 70.07 | |
| 28 | 106.17 | |

Figure 4N.

Cytokine/chemokine profiles induced in human PBMC cultures

| Compound No. | MIP-β(pg/ml) | MIP-β(pg/ml) |
|---|---|---|
|  | 10 μg/ml | 1 μg/ml |
| 22 | 280.93 |  |
| 23 |  | 5208.0 |
| 24 |  | 4595.8 |
| 25 | 1569.1 |  |
| 26 | 1214.1 |  |
| 27 | 95.7 |  |
| 28 | 450.9 |  |
| Media | 38.3 / 29.03 | 52.7 |

Cytokine/chemokine profiles induced in human PBMC cultures.

Cytokine/chemokine profiles induced in human PBMC cultures.

Cytokine/chemokine profiles induced in human PBMC cultures

Cytokine/chemokine profiles induced in human pDC cultures

Cytokine/chemokine profiles induced in human pDC cultures

Human B cell proliferation

Human B cell proliferation

Human B cell proliferation

Human B cell proliferation

Human B cell proliferation

Human B cell proliferation

In vivo induction of cytokines/chemokines by TLR9 agonists in C57Bl/6 mice

In vivo induction of IL-12 by TLR9 agonists in BALB/c mice

In vivo induction of IL-12 by TLR9 agonists in BALB/c mice

In vivo induction of IL-12 by TLR9 agonists in BALB/c mice

In vivo induction of IL-12 by TLR9 agonists in BALB/c mice

In vivo induction of IL-12 by TLR9 agonists in BALB/c mice

SYNTHETIC AGONISTS OF TLR9

RELATED APPLICATIONS

This application claims the benefit of U.S. Provisional Patent Application Ser. No. 60/953,251, filed on Aug. 1, 2007; U.S. Provisional Patent Application Ser. No. 60/983,601, filed on Oct. 30, 2007; U.S. Provisional Patent Application Ser. No. 60/987,151, filed on Nov. 12, 2007; and U.S. Provisional Patent Application Ser. No. 61/015,292, filed on Dec. 20, 2007, the entire contents of which are incorporated herein by reference.

BACKGROUND OF THE INVENTION

1. Field of the Invention

The invention relates to synthetic chemical compositions that are useful for modulation of Toll-Like Receptor (TLR)-mediated immune responses. In particular, the invention relates to agonists of Toll-Like Receptor 9 (TLR9) that generate unique cytokine and chemokine profiles.

2. Summary of the Related Art

Toll-like receptors (TLRs) are present on many cells of the immune system and have been shown to be involved in the innate immune response (Hornung, V. et al., (2002) J. Immunol. 168:4531-4537). In vertebrates, this family consists of eleven proteins called TLR1 to TLR11 that are known to recognize pathogen associated molecular patterns from bacteria, fungi, parasites, and viruses (Poltorak, a. et al. (1998) Science 282:2085-2088; Underhill, D. M., et al. (1999) Nature 401:811-815; Hayashi, F. et. al (2001) Nature 410: 1099-1103; Zhang, D. et al. (2004) Science 303:1522-1526; Meier, A. et al. (2003) Cell. Microbiol. 5:561-570; Campos, M. A. et al. (2001) J. Immunol. 167: 416-423; Hoebe, K. et al. (2003) Nature 424: 743-748; Lund, J. (2003) J. Exp. Med. 198:513-520; Heil, F. et al. (2004) Science 303:1526-1529; Diebold, S. S., et al. (2004) Science 303:1529-1531; Hornung, V. et al. (2004) J. Immunol. 173:5935-5943).

TLRs are a key means by which vertebrates recognize and mount an immune response to foreign molecules and also provide a means by which the innate and adaptive immune responses are linked (Akira, S. et al. (2001) Nature Immunol. 2:675-680; Medzhitov, R. (2001) Nature Rev. Immunol. 1: 135-145). Some TLRs are located on the cell surface to detect and initiate a response to extracellular pathogens and other TLRs are located inside the cell to detect and initiate a response to intracellular pathogens.

TLR9 is known to recognize unmethylated CpG motifs in bacterial DNA and in synthetic oligonucleotides. (Hemmi, H. et al. (2000) Nature 408:740-745). Other modifications of CpG-containing phosphorothioate oligonucleotides can also affect their ability to act as modulators of immune response through TLR9 (see, e.g., Zhao et al., Biochem. Pharmacol. (1996) 51:173-182; Zhao et al. (1996) Biochem Pharmacol. 52:1537-1544; Zhao et al. (1997) Antisense Nucleic Acid Drug Dev. 7:495-502; Zhao et al (1999) Bioorg. Med. Chem. Lett. 9:3453-3458; Zhao et al. (2000) Bioorg. Med. Chem. Lett. 10:1051-1054; Yu, D. et al. (2000) Bioorg. Med. Chem. Lett. 10:2585-2588; Yu, D. et al. (2001) Bioorg. Med. Chem. Lett. 11:2263-2267; and Kandimalla, E. et al. (2001) Bioorg. Med. Chem. 9:807-813). Naturally occurring agonists of TLR9 have been shown to produce anti-tumor activity (e.g. tumor growth and angiogenesis) resulting in an effective anti-cancer response (e.g. anti-leukemia) (Smith, J. B. and Wickstrom, E. (1998) J. Natl. Cancer Inst. 90:1146-1154). In addition, TLR9 agonists have been shown to work synergistically with other known anti-tumor compounds (e.g. cetuximab, irinotecan) (Vincenzo, D., et al. (2006) Clin. Cancer Res. 12(2):577-583).

Certain TLR9 agonists are comprised of 3'-3' linked DNA structures containing a core CpR dinucleotide, wherein the R is a modified guanosine (U.S. Pat. No. 7,276,489). In addition, specific chemical modifications have allowed the preparation of specific oligonucleotide analogs that generate distinct modulations of the immune response. In particular, structure activity relationship studies have allowed identification of synthetic motifs and novel DNA-based compounds that generate specific modulations of the immune response and these modulations are distinct from those generated by unmethylated CpG dinucleotides. (Kandimalla, E. et al. (2005) Proc. Natl. Acad. Sci. USA 102:6925-6930. Kandimalla, E. et al. (2003) Proc. Nat. Acad. Sci. USA 100:14303-14308; Cong, Y. et al. (2003) Biochem Biophys Res. Commun. 310:1133-1139; Kandimalla, E. et al. (2003) Biochem. Biophys. Res. Commun. 306:948-953; Kandimalla, E. et al. (2003) Nucleic Acids Res. 31:2393-2400; Yu, D. et al. (2003) Bioorg. Med. Chem. 11:459-464; Bhagat, L. et al. (2003) Biochem. Biophys. Res. Commun. 300:853-861; Yu, D. et al. (2002) Nucleic Acids Res. 30:4460-4469; Yu, D. et al. (2002) J. Med. Chem. 45:4540-4548. Yu, D. et al. (2002) Biochem. Biophys. Res. Commun. 297:83-90; Kandimalla. E. et al. (2002) Bioconjug. Chem. 13:966-974; Yu, D. et al. (2002) Nucleic Acids Res. 30:1613-1619; Yu, D. et al. (2001) Bioorg. Med. Chem. 9:2803-2808; Yu, D. et al. (2001) Bioorg. Med. Chem. Lett. 11:2263-2267; Kandimalla, E. et al. (2001) Bioorg. Med. Chem. 9:807-813; Yu, D. et al. (2000) Bioorg. Med. Chem. Lett. 10:2585-2588; Putta, M. et al. (2006) Nucleic Acids Res. 34:3231-3238).

The inventors have surprisingly discovered that uniquely modifying the sequence flanking the core CpR dinucleotide, the linkages between nucleotides or the linkers connecting the oligonucleotides produces novel agonists of TLR9 that generate distinct in vitro and in vivo cytokine and chemokine profiles. This ability to "custom-tune" the cytokine and chemokine response to a CpR containing oligonucleotide provides the ability to prevent and/or treat various disease conditions in a disease-specific and even a patient-specific manner. Thus, there is a need for new oligonucleotide analog compounds to provide such custom-tuned responses.

BRIEF SUMMARY OF THE INVENTION

The invention provides novel oligonucleotide-based compounds that individually provide distinct immune response profiles through their interactions as agonists with TLR9. The TLR9 agonists according to the invention are characterized by specific and unique chemical modifications, which provide their distinctive immune response activation profiles.

The TLR9 agonists according to the invention induce immune responses in various cell types and in various in vitro and in vivo experimental models, with each agonist providing a distinct immune response profile. The TLR9 agonists according to the invention are also useful in the prevention and/or treatment of various diseases, either alone, in combination with or co-administered with other drugs, or as adjuvants for antigens used as vaccines. As such, they are useful as tools to study the immune system, as well as to compare the immune systems of various animal species, such as humans and mice.

Thus, in a first aspect, the invention provides oligonucleotide-based agonists of TLR9 ("a compound").

In a second aspect, the invention provides pharmaceutical formulations comprising an oligonucleotide-based TLR9 agonist according to the invention and a pharmaceutically acceptable carrier.

In a third aspect, the invention provides a vaccine. Vaccines according to this aspect comprise a pharmaceutical formulation according to the invention and further comprise an antigen.

In a fourth aspect, the invention provides methods for generating a TLR9-mediated immune response in an individual, such methods comprising administering to the individual a compound, pharmaceutical formulation or vaccine according to the invention.

In a fifth aspect, the invention provides methods for therapeutically treating a patient having a disease or disorder, such methods comprising administering to the patient a compound, pharmaceutical formulation or vaccine according to the invention.

In a sixth aspect, the invention provides methods for preventing a disease or disorder, such methods comprising administering to the patient a compound, pharmaceutical formulation or vaccine according to the invention.

BRIEF DESCRIPTION OF THE DRAWINGS

FIGS. 3A-3G more generally demonstrate that administration of immune modulatory oligonucleotides containing novel bases, linkers, and/or unique modifications according to the invention generates distinct TLR9 activation profiles.

FIGS. 4A and 4B more generally demonstrate that administration of immune modulatory oligonucleotides containing novel bases, linkers, and/or unique modifications according to the invention generates distinct cytokine and chemokine profiles.

FIGS. 4C-4H more generally demonstrate that administration of immune modulatory oligonucleotides containing novel bases, linkers, and/or unique modifications according to the invention generates distinct cytokine and chemokine profiles.

FIGS. 4I-4N depict cytokine and chemokine concentrations from human PBMCs that were isolated, cultured, treated and analyzed according to Example 3 below. Briefly, the PBMCs were isolated from freshly obtained healthy human volunteer's blood and cultured with 0 (PBS), 1.0, or 10.0 μg/ml dose of immune modulatory oligonucleotides according to the invention for 24 hours. Supernatants were collected and analyzed by Luminex multiplex assay for cytokine and chemokine levels. FIGS. 4I-4N more generally demonstrate that administration of immune modulatory oligonucleotides containing novel bases, linkers, and/or unique modifications according to the invention generates distinct cytokine and chemokine profiles.

FIGS. 4O-4FF depict cytokine and chemokine concentrations from human PBMCs that were isolated, cultured, treated and analyzed according to Example 3 below. Briefly, the PBMCs were isolated from freshly obtained healthy human volunteer's blood and cultured with 0 (PBS), 0.1, 0.3, 1.0, 3.0, or 10.0 μg/ml dose of immune modulatory oligonucleotides according to the invention for 24 hours. Supernatants were collected and analyzed by Luminex multiplex assay for cytokine and chemokine levels. FIGS. 4O-4FF more generally demonstrate that administration of immune modulatory oligonucleotides containing novel bases, linkers, and/or unique modifications according to the invention generates distinct cytokine and chemokine profiles.

FIGS. 5A and 5B more generally demonstrate that administration of immune modulatory oligonucleotides containing novel bases, linkers, and/or unique modifications according to the invention generates distinct cytokine and chemokine profiles.

FIGS. 6A-6F more generally demonstrate that administration of immune modulatory oligonucleotides containing novel bases, linkers, and/or unique modifications according to the invention generates distinct cell proliferation profiles, which vary with the base composition, unique modification, and the amount of the oligonucleotide administered.

FIGS. 7A-7F more generally demonstrate that in vivo administration of immune modulatory oligonucleotides containing novel bases, linkers, and/or unique modifications according to the invention generates distinct TLR9 activation profiles, which will find application in a variety of diseases.

DETAILED DESCRIPTION OF THE PREFERRED EMBODIMENTS

Figure 1:
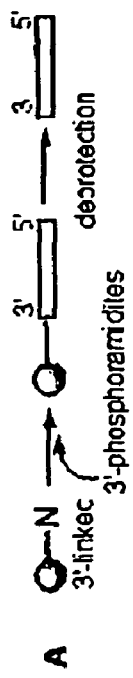
FIG. 1 is a synthetic scheme for the linear synthesis of immune modulatory compounds of the invention. DMTr=4,4'-dimethoxytrityl; CE=cyanoethyl.
Figure 1:
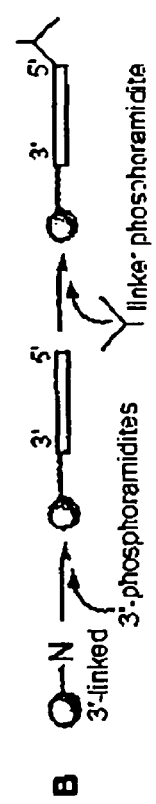
Figure 1:
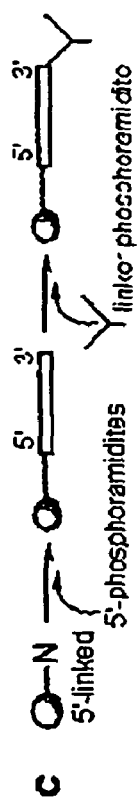
Figure 1:
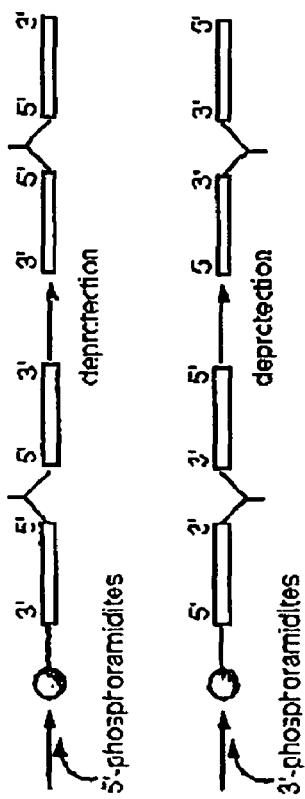
Figure 1:
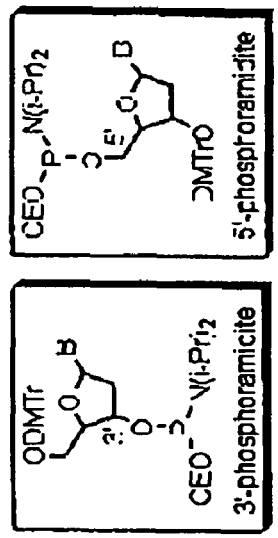
Figure 1:
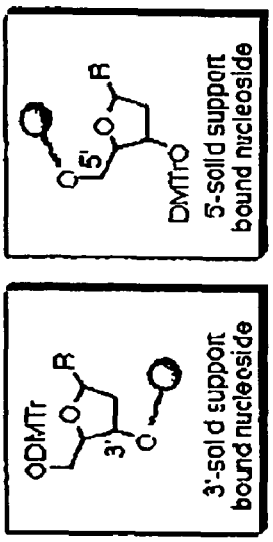

The invention provides novel oligonucleotide-based compounds that individually provide distinct immune response profiles through their interactions as agonists with TLR9. The TLR9 agonists according to the invention are characterized by unique chemical modifications, which provide their distinct immune response activation profiles. All publications cited herein reflect the level of skill in the art and are hereby incorporated by reference in their entirety. Any conflict between the teachings of these references and this specification shall be resolved in favor of the latter.

The TLR9 agonists according to the invention induce immune responses in various cell types and in various in vivo and in vitro experimental models, with each agonist providing a distinct immune response profile. As such, they are useful as tools to study the immune system, as well as to compare the immune systems of various animal species, such as humans and mice. The TLR9 agonists according to the invention are also useful in the prevention and/or treatment of various diseases, either alone, in combination with or co-administered with other drugs, or as adjuvants for antigens used as vaccines.

DEFINITIONS

The term "2'-substituted nucleoside" or "2'-substituted arabinoside" generally includes nucleosides or arabinonucleosides in which the hydroxyl group at the 2' position of a pentose or arabinose moiety is substituted to produce a 2'-substituted or 2'-O-substituted ribonucleoside. In certain embodiments, such substitution is with a lower hydrocarbyl group containing 1-6 saturated or unsaturated carbon atoms, with a halogen atom, or with an aryl group having 6-10 carbon atoms, wherein such hydrocarbyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-amino, 2'-fluoro, 2'-allyl, 2'-O-alkyl and 2'-propargyl ribonucleosides or arabinosides, 2'-O-methylribonucleosides or 2'-O-methylarabinosides and 2'-O-methoxyethoxyribonucleosides or 2'-O-methoxyethoxyarabinosides.

The term "3'", when used directionally, generally refers to a region or position in a polynucleotide or oligonucleotide 3' (toward the 3' position of the oligonucleotide) from another region or position in the same polynucleotide or oligonucleotide.

The term "5'", when used directionally, generally refers to a region or position in a polynucleotide or oligonucleotide 5' (toward the 5' position of the oligonucleotide) from another region or position in the same polynucleotide or oligonucleotide.

The term "about" generally means that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above.

The term "airway inflammation" generally includes, without limitation, inflammation in the respiratory tract caused by allergens, including asthma.

The term "allergen" generally refers to an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule.

The term "allergy" generally includes, without limitation, food allergies, respiratory allergies and skin allergies.

The term "antigen" generally refers to a substance that is recognized and selectively bound by an antibody or by a T cell antigen receptor. Antigens may include but are not limited to peptides, proteins, nucleosides, nucleotides and combinations thereof. Antigens may be natural or synthetic and generally induce an immune response that is specific for that antigen.

The term "autoimmune disorder" generally refers to disorders in which "self" antigen undergo attack by the immune system. Such term includes, without limitation, lupus erythematosus, multiple sclerosis, type I diabetes mellitus, irritable bowel syndrome, Chron's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis ("giant cell arteritis"), vasculitis, vitiligo, vulvodynia and Wegener's granulomatosis autoimmune asthma, septic shock, psoriasis and malaria.

The term "cancer" generally refers to, without limitation, any malignant growth or tumor caused by abnormal or uncontrolled cell proliferation and/or division. Cancers may occur in humans and/or animals and may arise in any and all tissues. Treating a patient having cancer with the invention may include administration of a compound, pharmaceutical formulation or vaccine according to the invention such that the abnormal or uncontrolled cell proliferation and/or division is affected.

The term "carrier" generally encompasses any excipient, diluent, filler, salt, buffer, stabilizer, solubilizer, oil, lipid, lipid containing vesicle, microspheres, liposomal encapsulation, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., *Remington's Pharmaceutical Sciences,* 18th Edition, ed. A. Gennaro, Mack Publishing Co., Easton, Pa., 1990.

The term "pharmaceutically acceptable" or "physiologically acceptable" generally refers to a material that does not interfere with the effectiveness of a compound according to the invention, and that is compatible with a biological system such as a cell, cell culture, tissue, or organism. Preferably, the biological system is a living organism, such as a vertebrate.

The term "co-administration" or "co-administered" generally refers to the administration of at least two different substances sufficiently close in time to modulate an immune response. Preferably, co-administration refers to simultaneous administration of at least two different substances.

The term a "pharmaceutically effective amount" generally refers to an amount sufficient to affect a desired biological effect, such as a beneficial result. Thus, a "pharmaceutically effective amount" will depend upon the context in which it is being administered. A pharmaceutically effective amount may be administered in one or more prophylactic or therapeutic administrations.

The term "in combination with" generally means administering a compound according to the invention and another agent useful for treating the disease or condition that does not abolish TLR9 antagonist effect of the compound in the course of treating a patient. Such administration may be done in any order, including simultaneous administration, as well as temporally spaced order from a few seconds up to several days apart. Such combination treatment may also include more than a single administration of the compound according to the invention and/or independently the other agent. The administration of the compound according to the invention and the other agent may be by the same or different routes.

The term "individual" or "subject" generally refers to a mammal, such as a human. Mammals generally include, but are not limited to, humans, non-human primates, rats, mice, cats, dogs, horses, cattle, cows, pigs, sheep and rabbits.

The term "kinase inhibitor" generally refers to molecules that antagonize or inhibit phosphorylation-dependent cell signaling and/or growth pathways in a cell. Kinase inhibitors may be naturally occurring or synthetic and include small molecules that have the potential to be administered as oral therapeutics. Kinase inhibitors have the ability to rapidly and specifically inhibit the activation of the target kinase molecules. Protein kinases are attractive drug targets, in part because they regulate a wide variety of signaling and growth pathways and include many different proteins. As such, they have great potential in the treatment of diseases involving kinase signaling, including cancer, cardiovascular disease, inflammatory disorders, diabetes, macular degeneration and neurological disorders. Examples of kinase inhibitors include sorafenib (Nexavar®), Sutent®, dasatinib, Dasatinib™, Zactima™, Tykerb™ and STI571.

The term "linear synthesis" generally refers to a synthesis that starts at one end of an oligonucleotide and progresses linearly to the other end. Linear synthesis permits incorporation of either identical or non-identical (in terms of length, base composition and/or chemical modifications incorporated) monomeric units into an oligonucleotide.

The term "mammal" is expressly intended to include warm blooded, vertebrate animals, including, without limitation, humans.

The term "modified nucleoside" generally is a nucleoside that includes a modified heterocyclic base, a modified sugar moiety, or any combination thereof. In some embodiments, the modified nucleoside is a non-natural pyrimidine or purine nucleoside, as herein described. For purposes of the invention, a modified nucleoside, a pyrimidine or purine analog or non-naturally occurring pyrimidine or purine can be used interchangeably and refers to a nucleoside that includes a non-naturally occurring base and/or non-naturally occurring sugar moiety. For purposes of the invention, a base is considered to be non-natural if it is not guanine, cytosine, adenine, thymine or uracil.

The term "modulation" or "modulatory" generally refers to change, such as an increase in a response or qualitative difference in a TLR9-mediated response.

The term "linker" generally refers to any moiety that can be attached to an oligonucleotide by way of covalent or non-covalent bonding through a sugar, a base, or the backbone. The linker can be used to attach two or more nucleosides or can be attached to the 5' and/or 3' terminal nucleotide in the oligonucleotide. In certain embodiments of the invention, such linker may be a non-nucleotidic linker.

The term "non-nucleotidic linker" generally refers to a chemical moiety other than a nucleotidic linkage that can be attached to an oligonucleotide by way of covalent or non-covalent bonding. Preferably such non-nucleotidic linker is from about 2 angstroms to about 200 angstroms in length, and may be either in a cis or trans orientation.

The term "nucleotidic linkage" generally refers to a chemical linkage to join two nucleosides through their sugars (e.g. 3'-3',2'-3',2'-5',3'-5') consisting of a phosphorous atom and a charged, or neutral group (e.g., phosphodiester, phosphorothioate or phosphorodithioate) between adjacent nucleosides.

The term "oligonucleotide-based compound" refers to a polynucleoside formed from a plurality of linked nucleoside units. The nucleoside units may be part of or may be made part of viruses, bacteria, cell debris, siRNA or microRNA. Such oligonucleotides can also be obtained from existing nucleic acid sources, including genomic or cDNA, but are preferably produced by synthetic methods. In preferred embodiments each nucleoside unit includes a heterocyclic base and a pentofuranosyl, trehalose, arabinose, 2'-deoxy-2'-substituted nucleoside, 2'-deoxy-2'-substituted arabinose, 2'-O-substitutedarabinose or hexose sugar group. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide-based compound" also encompasses polynucleosides having one or more stereospecific internucleoside linkage (e.g., ($R_p$)— or ($S_p$)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate or phosphorodithioate linkages, or combinations thereof.

The term "peptide" generally refers to polypeptides that are of sufficient length and composition to affect a biological response, e.g., antibody production or cytokine activity whether or not the peptide is a hapten. The term "peptide" may include modified amino acids (whether or not naturally or non-naturally occurring), where such modifications include, but are not limited to, phosphorylation, glycosylation, pegylation, lipidization and methylation.

The term "TLR9 agonist" generally refers to an oligonucleotide-based compound that is able to enhance, induce or modulate an immune stimulation mediated by TLR9.

The term "treatment" generally refers to an approach intended to obtain a beneficial or desired result, which may include alleviation of symptoms, or delaying or ameliorating a disease progression.

Certain TLR9 agonists according to the invention are shown in Table I below. In this table, the oligonucleotide-based TLR9 agonists have all phosphorothioate (PS) linkages, except where indicated. Those skilled in the art will recognize, however, that phosphodiester (PO) linkages, or a mixture of PS and PO linkages can be used. Except where indicated, all nucleotides are deoxyribonucleotides.

TABLE I

| (Seq. ID. No.)/ Compound No. | | Sequence and Modifications |
|---|---|---|
| 1 | (1) | 5'-TCG$_1$TACG$_1$TACG$_1$-X-G$_1$CATG$_1$CATG$_1$CT-5' |
| 2 | (2) | 5'-TCTGT$_O$CG$_2$TTGT-X-TGTTG$_2$C$_O$TGTCT-5' |
| 3 | (3) | 5'-TCAGT$_O$CG$_2$TTAC-Z-CATTG$_2$C$_O$TGACT-5' |
| 4 | (4 & 170) | 5'-TCTG$_O$T$_O$CG$_2$TAG-M-GATTG$_2$C$_O$T$_O$GTCT-5' |
| 5 | (5) | 5'-TCG$_1$TCG$_1$TTT-L-M-L-TTTG$_1$CTG$_1$CT-5' |
| 6 | (6) | 5'-TCG$_1$TCG$_1$TTT-L-X-L-TTTG$_1$CTG$_1$CT-5' |
| 7 | (7) | 5'-TCG$_1$AACG$_1$TTCo<u>G</u>-Z-<u>G</u>oCTTG$_1$CAAG$_1$CT-5' |
| 8 | (8 & 18) | 5'-TCG$_1$TCG$_1$TTL-Y-G$_1$CTTG$_1$CAAG$_1$CT-5' |
| 9 | (9) | 5'-TCTGTCG$_2$TT<u>CU</u>-X-<u>UC</u>TTG$_2$CTGTCT-5' |
| 10 | (10) | 5'-TCG$_1$TCG$_1$TTT<u>UU</u>-X-<u>UU</u>TTTG$_1$CTG$_1$CT-5' |
| 11 | (11) | 5'-TCG$_1$TCG$_1$TTU$_1$Y-Z-YU$_1$TTG$_1$CTG$_1$CT-5' |
| 12 | (12) | 5'-TCG$_2$TCG$_2$TTU$_1$Y-M-YU$_1$TTG$_2$CTG$_2$CT-5' |
| 13 | (13) | 5'-TAGTCG$_1$TTCTC-X-CTCTTG$_1$CTGAT-5' |
| 14 | (14) | 5'-TC<u>U</u>TGTCG$_1$TTC-X-CTTG$_1$CTGT<u>U</u>CT-5' |
| 15 | (15 & 171) | 5'-TCG$_1$TCG$_1$TTTTT-Y-TCTTG$_1$CTG<u>U</u>CT-5' |
| 16 | (16 & 172) | 5'-TCG$_1$TCG$_1$TTTTT-Y-TCTTG$_1$CTGT<u>C</u>TTG$_1$CT-5' |
| 17 | (17) | 5'-TCTGTCG$_1$TTCT-Y-TCTTG$_1$CTGYYTTG$_1$CT-5' |
| 18 | (18 & 172) | 5'-TCG$_1$AACG$_1$TTCG$_1$-Y-TCTTG$_1$CTGT<u>C</u>TTG$_1$CT-5' |
| 19 | (19) | 5'-TCG$_1$AACG$_1$TTCG$_1$-Y-TCTTG$_1$CTG<u>LL</u>TTG$_1$CT-5' |
| 20 | (20 & 171) | 5'-TCG$_1$AACG$_1$TTCG$_1$-Y-TCTTG$_1$CTG<u>U</u>CT-5' |
| 21 | (21 & 173) | 5'-TCG$_1$AACG$_1$TTCG$_1$-Y-<u>GA</u>CAG$_1$CTGTCT-5' |
| 22 | (22) | 5'-TCTGTCG$_1$TTCT-m-TCTTG$_1$CTGTCT-5' |
| 23 | (23) | 5'-CAGTC$_O$G$_2$TTCAG-M-GACTTG$_{2O}$CTGAC-5' |
| 24 | (24 & 18) | 5'-CAGTC$_O$G$_2$TTCAG-Y-G$_1$CTTG$_1$CAAG$_1$CT-5' |
| 25 | (25) | 5'-TCG$_1$AACG$_1$TTC<u>G</u>-Z-<u>G</u>CTTG$_1$CAAG$_1$CT-5' |
| 26 | (26 & 174) | 5'-TCG$_1$TCG$_1$TTTTT-Y-TCTTG$_1$CTG<u>UC</u>T-5' |
| 27 | (27) | 5'-TCG$_2$TC$_O$G$_2$TTU$_1$Y-X-YU$_1$TTG$_{2O}$CTG$_2$CT-5' |
| 28 | (28) | 5'-TCG$_1$AACG$_1$U$_1$U$_1$C<u>G</u>-X-<u>Gc</u>U$_1$U$_1$G$_1$CAAG$_1$CT-5' |
| 29 | (29) | 5'-TCTGTCG$_1$TTCT-L$_1$-TCTTG$_1$CTGTCT-5' |
| 30 | (30 & 18) | 5'-CAGTCG$_2$TTCAG-Y-G$_1$CTTG$_1$CAAG$_1$CT-5' |

TABLE I-continued

| (Seq. ID. No.)/ Compound No. | Sequence and Modifications |
|---|---|
| 31 (31) | 5'-CAGTCoG$_2$TTCAG-Z-GACTTG$_2$oCTGAC-5' |
| 32 (32 & 175) | 5'-TCTGTCG$_1$TTCT-Y-TCTTG$_2$CTGU̲CTTG$_1$CT-5' |
| 33 (33) | 5'-TCG$_1$AACG$_1$U$_1$U$_1$CoG̲-M-G̲oCU$_1$U$_1$G$_1$CAAG$_1$CT-5' |
| 34 (34) | 5'-TCG$_1$AACG$_1$ToTCoG̲-m-G̲oCToTG$_1$CAAG$_1$CT-5' |
| 35 (35) | 5'-TCG$_1$AACG$_1$TTCG$_1$-L$_1$-G$_1$CTTG$_1$CAAG$_1$CT-5' |
| 36 (36) | 5'-CAGTCG$_2$TTCAG-X$_1$-GACTTG$_2$CTGAC-5' |
| 37 (37) | 5'-CAGTCG$_2$TTCAG-X$_2$-GACTTG$_2$CTGAC-5' |
| 38 (38) | 5'-psCAGTCG$_2$TTCAG-X-GACTTG$_2$CTGACps-5' |
| 39 (39 & 30) | 5'-TCG$_1$AACG$_1$TTCoG$_1$-Y$_2$-GACTTG$_2$CTGAC-5' |
| 40 (40 & 30) | 5'-TCG$_1$AACG$_1$TTCG̲-Y$_2$-GACTTG$_2$CTGAC-5' |
| 41 (41 & 30) | 5'-TCG$_1$AACG$_1$TTCoG̲-Y$_2$-GACTTG$_2$CTGAC-5' |
| 42 (42 & 176) | 5'-TCG$_1$AACG$_1$TTCoG̲-Y$_2$-CTTG$_2$CTGAC̲UTG$_1$CT-5' |
| 43 (43 & 17) | 5'-CAGTCG$_2$TTCAG-Y$_2$-TCTTG$_1$CTGTCT-5' |
| 44 (44 & 177) | 5'-TCG$_1$AACG$_1$TTCoG̲-Y$_2$-CTTG$_2$CTGApmCTTG$_1$CT-5' |
| 45 (45 & 178) | 5'-TCG$_1$AACG$_1$TTCG1-Y$_3$-TGTTG$_1$CTGTC̲TTG$_1$CT-5' |
| 46 (46) | 5'-TCAGTCG$_1$TTAC-X-CATTG$_1$CTGACT-5' |
| 47 (47) | 5'-TCTGTCG$_1$TTTT-X-TTTTG$_1$CTGTCT-5' |
| 48 (48) | 5'-TCAGTCG$_1$TTACY$_1$-X$_3$-Y$_1$CATTG$_1$CTGACT-5' |
| 49 (49) | 5'-TCTGTCG$_1$TTTTY$_1$-X$_3$-Y$_1$TTTTG$_1$CTGTCT-5' |
| 50 (50 & 18) | 5'-TCG$_1$TCG$_1$TTY$_3$-Y-G$_1$CTTG$_1$CAAG$_1$CT-5' |
| 51 (51) | 5'-TCG$_1$TCG$_1$TTdUY-Z-YdUTTG$_1$CTG$_1$CT-5' |
| 52 (52) | 5'-TCG$_1$TCG$_1$TTdUY-X-YdUTTG$_1$CTG$_1$CT-5' |
| 53 (53) | 5'-TCG$_1$TCG$_1$TTdUY-M-YdUTTG$_1$CTG$_1$CT-5' |
| 54 (54) | 5'-TCG$_1$TCG$_1$TTdUY-m-YdUTTG$_1$CTG$_1$CT-5' |
| 55 (55) | 5'-TCG$_2$TCG$_2$TTdUY-Z-YdUTTG$_2$CTG$_2$CT-5' |
| 56 (56) | 5'-TCG$_2$TCG$_2$TTdUY-X-YdUTTG$_2$CTG$_2$CT-5' |
| 57 (57) | 5'-TCG$_2$TCG$_2$TTdUY-M-YdUTTG$_2$CTG$_2$CT-5' |
| 58 (58) | 5'-TCG$_2$TCG$_2$TTdUY-m-YdUTTG$_2$CTG$_2$CT-5' |
| 59 (59) | 5'-TCG$_1$TCG$_1$ACG$_1$AT-Z-TAG$_1$CAG$_1$CTG$_1$CT-5' |
| 60 (60) | 5'-TCAGTCG$_2$TTAC-X-CATTG$_2$CTGACT-5' |
| 61 (61) | 5'-TCG$_1$ATCG$_1$ATCG$_1$-X-G$_1$CTAG$_1$CTAG$_1$CT-5' |
| 62 (62) | 5'-TCG$_1$AACG$_1$TTCG$_1$-Z-G$_1$CTTG$_1$CAAG$_1$CT-5' |
| 63 (63) | 5'-TCG$_1$AACG$_1$TTCG̲-Z-G̲CTTG$_1$CAAG$_1$CT-5' |
| 64 (64 & 173) | 5'-TCG$_1$AACG$_1$TTCG$_1$-Y-GA̲CAG$_1$CTGTCT-5' |
| 65 (65 & 179) | 5'-TAGTCG$_1$TTTTT-X-TTTTTG$_1$CGTAT-5' |
| 66 (66) | 5'-TCGTCGTTCTT-X-TTCTTGCTGCT-5' |
| 67 (67) | 5'-TGGTCG$_2$TTCTT-X-TTCTTG$_2$CTGGT-5' |
| 68 (68) | 5'-TAGTCG$_2$TTCTC-X-CTCTTG$_2$CTGAT-5' |

TABLE I-continued

| (Seq. ID. No.)/ Compound No. | Sequence and Modifications |
|---|---|
| 69 (69 & 180) | 5'-TCG$_1$TCG$_1$TTTTT-Y-TCTTG$_1$CTGT<u>C</u>T-5' |
| 70 (70 & 174) | 5'-TCG$_1$TCG$_1$TTTTT-Y-TCTTG$_1$CTG<u>U</u>CT-5' |
| 71 (71 & 181) | 5'-TCG$_1$TCG$_1$TTTTT-Y-TCTTG$_1$CTGT<u>C</u>TTCCT-5' |
| 72 (72) | 5'-TCTTGTCG$_1$TTC-X-CTTG$_1$CTGTTCT-5' |
| 73 (73) | 5'-TCTTGTCG$_1$TTC-X-CTTG$_1$CTGTT<u>C</u>T-5' |
| 74 (74) | 5'-TCTGTCG$_3$TTCT-X-TCTTG$_3$CTGTCT-5' |
| 75 (75) | 5'-TCG$_3$AACG$_3$TTCG$_3$-X-G$_3$CTTG$_3$CAAG$_3$CT-5' |
| 76 (76 & 175) | 5'-TCG$_1$TCG$_1$TTTTT-X-TCTTG$_1$CTG<u>U</u>CTTG$_1$CT-5' |
| 77 (77) | 5'-TCG$_1$TCG$_1$TTTTT-X-TCTTG$_1$CTGYYTTG$_1$CT-5' |
| 78 (78) | 5'-TCG$_1$TCG$_1$TTTTT-X-TCTTG$_1$CTG<u>LL</u>TTG$_1$CT-5' |
| 79 (79) | 5'-TCTGTCG$_1$TTCT-Y-TCTTG$_1$CTG<u>LL</u>TTG$_1$CT-5' |
| 80 (80 & 171) | 5'-TCG$_1$AACG$_1$TTCG$_1$-<u>L</u>-TCTTG$_1$CTG<u>U</u>CT-5' |
| 81 (81) | 5'-CAGTCG$_2$TTCAG-X-GACTTG$_2$CTGAC-5' |
| 82 (82 & 182) | 5'-CAGTCG$_2$TTCAG-Z-GACTTG$_2$CTTAC-5' |
| 83 (83 & 182) | 5'-CAGTCG$_2$TTCAG-M-GACTTG$_2$CTTAC-5' |
| 84 (84 & 182) | 5'-CAGTCG$_2$TTCAG-m-GACTTG$_2$CTTAC-5' |
| 85 (85 & 183) | 5'-CAGTCoG$_2$TTCAG-X-GACTTG$_2$CoTTAC-5' |
| 86 (86 & 183) | 5'-CAGTCoG$_2$TTCAG-M-GACTTG$_2$CoTTAC-5' |
| 87 (87 & 183) | 5'-CAGTCoG$_2$TTCAG-m-GACTTG$_2$CoTTAC-5' |
| 88 (88 & 18) | 5'-CAGTCoG$_2$TTCAG-Y-G$_1$CTTG$_1$CAAG$_1$CT-5' |
| 89 (89) | 5'-TCG$_1$AACG$_1$ToTCoG$_1$-m-G$_1$oCToTG$_1$CAAG$_1$CT-5' |
| 90 (90) | 5'-TCG$_1$AACG$_1$oTTCG$_1$-Z-G$_1$CTToG$_1$CAAG$_1$CT-5' |
| 91 (91) | 5'-TCG$_1$AACG$_1$oToTCoG-Z-<u>G</u>oCoToToG$_1$CAAG$_1$CT-5' |
| 92 (92) | 5'-TCG$_1$AACoG$_1$TTCG$_1$-X-G$_1$CTTG$_1$oCAAG$_1$CT-5' |
| 93 (93) | 5'-TCG$_1$AACG$_1$dUdUCG$_1$-X-G$_1$CdUdUG$_1$CAAG$_1$CT-5' |
| 94 (94) | 5'-TCG$_1$AACG$_1$dUdUCoG-X-<u>G</u>oCdUdUG$_1$CAAG$_1$CT-5' |
| 95 (95) | 5'-TCG$_1$AACG$_1$dUdUCoG-Z-<u>G</u>oCdUdUG$_1$CAAG$_1$CT-5' |
| 96 (96) | 5'-TCG$_1$AACG$_1$dUdUCoG-m-<u>G</u>oCdUdUG$_1$CAAG$_1$CT-5' |
| 97 (97) | 5'-TCG$_1$AACG$_1$dUdUC<u>G</u>-X-<u>G</u>CdUdUG$_1$CAAG$_1$CT-5' |
| 98 (98) | 5'-TCG$_1$AACG$_1$TTCG$_1$-L$_2$-G$_1$CTTG$_1$CAAG$_1$CT-5' |
| 99 (99 & 184) | 5'-TCG$_1$TCG$_1$TTCT-L$_3$-TCTTG$_1$CTGG$_1$CT-5' |
| 100 (100 & 185) | 5'-TCTG$_1$TCG$_1$TTCG$_1$-L$_3$-M-L$_3$-G$_1$CTTG$_1$CTGTCT-5' |
| 101 (101) | 5'-TCG$_1$GTCG$_1$TTCG$_1$-L$_3$-m-L$_3$-G$_1$CTTG$_1$CTGG$_1$CT-5' |
| 102 (102) | 5'-TCTGTCG$_1$TTCT-L$_2$-TCTTG$_1$CTGTCT-5' |
| 103 (103) | 5'-TCTGTCG$_1$TTCT-L$_3$-TCTTG$_1$CTGTCT-5' |
| 104 (104) | 5'-TCTGTCG$_1$TTCT-L$_3$-M-L$_3$-TCTTG$_1$CTGTCT-5' |
| 105 (105) | 5'-TCTGTCG$_1$TTCT-L$_3$-m-L$_3$-TCTTG$_1$CTGTCT-5' |
| 106 (106) | 5'-CAGTCG$_3$TTCAG-X-GACTTG$_3$CTGAC-5' |
| 107 (107) | 5'-TCTGTCG$_3$TTCT-X-TCTTG$_3$CTGTCT-5' |

TABLE I-continued

| (Seq. ID. No.)/ Compound No. | Sequence and Modifications |
|---|---|
| 108 (108) | 5'-TCTGTCG$_1$TTCT-X$_1$-TCTTG$_1$CTGTCT-5' |
| 109 (109) | 5'-TCTGTCG$_1$TTCT-X$_2$-TCTTG$_1$CTGTCT-5' |
| 110 (110) | 5'-TCTGTCG$_1$TTCT-Z-TCTTG$_1$CTGTCT-5' |
| 111 (111) | 5'-TCTGTCG$_1$TTCT-M-TCTTG$_1$CTGTCT-5' |
| 112 (112) | 5'-TCTGTCG$_1$TTCT-m-TCTTG$_1$CTGTCT-5' |
| 113 (113) | 5'-TCG$_1$AACG$_1$TTCG$_1$-Z-G$_1$CTTG$_1$CAAG$_1$CT-5' |
| 114 (114) | 5'-TCG$_1$AACG$_1$TTCG$_1$-M-G$_1$CTTG$_1$CAAG$_1$CT-5' |
| 115 (115) | 5'-TCG$_1$AACG$_1$TTCG$_1$-m-G$_1$CTTG$_1$CAAG$_1$CT-5' |
| 116 (116) | 5'-TCG$_1$AACG$_1$TTCG$_1$-X$_2$-G$_1$CTTG$_1$CAAG$_1$CT-5' |
| 117 (117) | 5'-TCG$_1$AACG$_1$TTCG$_1$-X$_1$-G$_1$CTTG$_1$CAAG$_1$CT-5' |
| 118 (118) | 5'-Y$_1$CAGTCG$_2$TTCAG-X-GACTTG$_2$CTGACY$_1$-5' |
| 119 (119) | 5'-YCAGTCG$_2$TTCAG-X-GACTTG$_2$CTGACY-5' |
| 120 (120) | 5'-poCAGTCG$_2$TTCAG-X-GACTTG$_2$CTGACpo-5' |
| 121 (121 & 22) | 5'-CAGTCG$_2$TTCAG-Y$_2$-TCTTG$_1$CTGTCT-5' |
| 122 (122 & 186) | 5'-TCG$_1$AACG$_1$TTCo<u>G</u>-Y$_2$-CTTG$_2$CTGA<u>C</u>TTG$_1$CT-5' |
| 123 (123) | 5'-TCAGTCG$_1$TTAC-X-CATTG$_1$CTGACT-5' |
| 124 (124) | 5'-TCTGTCG$_1$TTAG-X-GATTG$_1$CTGTCT-5' |
| 125 (125) | 5'-TCTGTCG$_1$TTTT-X-TTTTG$_1$CTGTCT-5' |
| 126 (126) | 5'-TCTGTCG$_1$TTGT-X-TGTTG$_1$CTGTCT-5' |
| 127 (127 & 186) | 5'-TCG$_1$AACG$_1$TTCo<u>G</u>-Y$_2$-CTTG$_2$CTGA<u>C</u>TTG$_1$CT-5' |
| 128 (128) | 5'-TCG$_1$AACG$_1$oTTCG$_1$-Z-G$_1$CTToG$_1$CAAG$_1$CT-5' |
| 129 (129) | 5'-TCG$_1$AACG$_1$TTCG$_1$-X$_2$-G$_1$CTTG$_1$CAAG$_1$CT-5' |
| 130 (130 & 177) | 5'-TCG$_1$AACG$_1$TTCo<u>G</u>-Y$_2$-CTTG$_2$CTGApmCTTG$_1$CT-5' |
| 131 (131 & 187) | 5'-TCG$_1$AACG$_1$TTCo<u>G</u>-Y$_2$-CTTG$_2$CTGApmCpmTTG$_1$CT-5' |
| 132 (132 & 180) | 5'-TCG$_1$TCG$_1$TTTTT-Y$_3$-TCTTG$_1$CTGT<u>C</u>T-5' |
| 133 (133 & 181) | 5'-TCG$_1$TCG$_1$TTTTT-Y$_3$-TCTTG$_1$CTGT<u>C</u>TTCCT-5' |
| 134 (134) | 5'-TCG$_2$TCG$_2$TTdUY$_3$-X$_3$-Y$_3$dUTTG$_2$CTG$_2$CT-5' |
| 135 (135) | 5'-TCG$_1$AACG$_1$oTTCG$_1$-X$_3$-G$_1$CTToG$_1$CAAG$_1$CT-5' |
| 136 (136) | 5'-TCTGTCG$_1$TTAC-Y$_3$-CATTG$_1$CTGYYTTG$_1$CT-5' |
| 137 (137) | 5'-TCTGTCG$_1$TTGT-Y$_3$-TGTTG$_1$CTGYYTTG$_1$CT-5' |
| 138 (138) | 5'-TCAGTCG$_1$TTCT-Y$_3$-CATTG$_1$CTGYYTTG$_1$CT-5' |
| 139 (139 & 188) | 5'-TCG$_1$AACG$_1$TTCG$_1$-Y$_3$-CATTG$_1$CTGT<u>C</u>TTG$_1$CT |
| 140 (140 & 178) | 5'-TCG$_1$AACG$_1$TTCG$_1$-Y$_3$-TGTTG$_1$CTGT<u>C</u>TTG$_1$CT |
| 141 (141 & 189) | 5'-TCTGTCG$_1$TTAC-Y$_3$-TGTTG$_1$CTG<u>UC</u>TTG$_1$CT-5' |
| 142 (142 & 190) | 5'-TCTGTCG$_1$TTGT-Y$_3$-AGTTG$_1$CTG<u>UC</u>TTG$_1$CT-5' |
| 143 (143 & 191) | 5'-TCAGTCG$_1$TTAG-Y$_3$-CATTG$_1$CTG<u>UC</u>TTG$_1$CT-5' |
| 144 (144) | 5'-TCAGTCG$_1$TTAC-X-CATTG$_1$CTGACT-5' |
| 145 (145) | 5'-TCTGTCG$_1$TTAG-X-GATTG$_1$CTGTCT-5' |

TABLE I-continued

| (Seq. ID. No.)/ Compound No. | Sequence and Modifications |
|---|---|
| 146 (146) | 5'-TCTGTCG$_1$TTTT-X-TTTTG$_1$CTGTCT-5' |
| 147 (147) | 5'-TCTGTCG$_1$TTGT-X-TGTTG$_1$CTGTCT-5' |
| 148 (148) | 5'-Y$_1$CAGTCG$_2$TTCAG-X-GACTTG$_2$CTGACY$_1$-5' |
| 149 (149) | 5'-TCAGTCG$_1$TTACY$_1$-X$_3$-Y$_1$CATTG$_1$CTGACT-5' |
| 150 (150) | 5'-TCTGTCG$_1$TTAGY$_1$-X$_3$-Y$_1$GATTG$_1$CTGTCT-5' |
| 151 (151) | 5'-TCTGTCG$_1$TTTTY$_1$-X$_3$-Y$_1$TTTTG$_1$CTGTCT-5' |
| 152 (152) | 5'-TCTGTCG$_1$TTGTY$_1$-X$_3$-Y$_1$TGTTG$_1$CTGTCT-5' |
| 153 (153) | 5'-TCG$_1$AACG$_1$oTTCG$_1$-Z-G$_1$CTToG$_1$CAAG$_1$CT-5' |
| 154 (154) | 5'-TCG$_1$AACG$_1$TTCG$_1$-X$_2$-G$_1$CTTG$_1$CAAG$_1$CT-5' |
| 155 (155) | 5'-TCG$_1$TACG$_1$TACG$_1$-X$_1$-G$_1$CATG$_1$CATG$_1$CT-5' |
| 156 (156) | 5'-TCG$_1$TACG$_1$TACG$_1$-X$_3$-G$_1$CATG$_1$CATG$_1$CT-5' |
| 157 (157) | 5'-TCG$_1$TACG$_1$TACG$_1$-X-G$_1$CATG$_1$CATG$_1$CT-5' |
| 158 (158 & 29) | 5'-CAGTCG$_2$TTCAG-Y$_2$-TCTTG$_1$CTGTCT-5' |
| 159 (159 & 179) | 5'-TAGTCG$_1$TTTTT-X-TTTTTG$_1$CGTAT-5' |
| 160 (160) | 5'-TCTGTCG$_1$TTCT-Z-TCTTG$_1$CTGTCT-5' |
| 161 (161) | 5'-TCTGTCG$_1$TTCT-M-TCTTG$_1$CTGTCT-5' |
| 162 (162) | 5'-TCTGTCG$_1$TTCT-L$_2$-TCTTG$_1$CTGTCT-5' |
| 163 (163) | 5'-TCG$_1$AACG$_1$oTTCG$_1$-Z-G$_1$CTToG$_1$CAAG$_1$CT-5' |
| 164 (164) | 5'-TCG$_1$AACG$_1$TTCG$_1$-X$_2$-G$_1$CTTG$_1$CAAG$_1$CT-5' |
| 165 (165) | 5'-TCG$_1$AACG$_1$TTCG$_1$-m-G$_1$CTTG$_1$CAAG$_1$CT-5' |
| 166 (166) | 5'-TCG$_1$AACG$_1$ToTCoG-m-GoCToTG$_1$CAAG$_1$CT-5' |
| 167 (167) | 5'-TCG$_1$AACG$_1$dUdUCo$\underline{G}$-M-$\underline{G}$CodUdUG$_1$CAAG$_1$CT-5' |
| 168 (168) | 5'-TCG$_1$TCG$_1$ACG$_1$AT-X-TAG$_1$CAG$_1$CTG$_1$CT-5' |
| 169 (169) | 5'-TCG$_1$ATCG$_1$ATCG$_1$-X-G$_1$CTAG$_1$CTAG$_1$CT-5' |

$G_1$=7-deaza-dG; $G_2$=AraG; $G_3$=7-deaza-araG; A/G/C/U=2'-O-methylribonucleotides; dU=U$_1$=2'-$\overline{deoxy}$-$\overline{U}$; o=phosphodiester linkage; po=5'-mono-phosphate; ps=5'phosphorothiate linkage; pm=methyl phosphonate (non-ionic linkage); L=1,5-pentanediol linker; L=1,2-dideoxyribose; L$_1$=triethylene glycol linker; L$_2$=tetraethylene glycol linker; L$_3$=hexaethylene glycol linker M=cis,cis-1,3,5-cyclohexanetriol linker; m=cis,trans-1,3,5-cyclohexanetriol linker; X=glycerol linker; X$_1$=1,2,4-butanetriol linker; X$_2$=1,3,5-tris(2-hydroxyethyl)cyanuric acid linker; X$_3$=isobutanetriol linker; Y=1,3-propanediol linker; Y$_1$=1,2-ethylenediol linker; Y$_2$=1,4-butanediol linker; Y$_3$=1,5-pentandiol linker; Z=1,3,5-pentanetriol linker.

Exemplar TLR9 agonists from Table I were tested for immune stimulatory activity in HEK293 cells expressing TLR9, as described in Example 2. The results shown in FIGS. 3A, 3B, 3C, 3D, and 3E demonstrate that specific chemical modifications to 3'-3' linked oligonucleotides will alter their TLR9 mediated NF-kB activation profile 18 hours after administration. More generally, these data demonstrate that specific chemical modifications to 3'-3' linked oligonucleotides can be used to increase or decrease NF-kB activation.

Exemplar TLR9 agonists from Table I were tested for immune stimulatory activity in the human PBMC assay for IL-12, IL-10, IL-8, IL-6, IFN-α, IP-10, MIP-1α, MIP-1β, IL-1Rα, IL-2R, and MCP-1, as described in Example 3. The results shown in FIGS. 4A through 4FF demonstrate that specific chemical modifications to 3'-3' linked oligonucleotides will alter their TLR9 mediated IL-12, IL-10, IL-8, IL-6, IFN-α, IP-10, MIP-1α, MIP-1β, IL-1Rα, IL-2R, and/or MCP-1 activation profile in human PBMCs. More generally, these data demonstrate that specific chemical modifications to 3'-3' linked oligonucleotides can be used to increase or decrease IL-12, IL-10, IL-8, IL-6, IFN-α, IP-10, MIP-1α, MIP-1β, IL-1Rα, IL-2R, and MCP-1 activation.

Figure 5A:
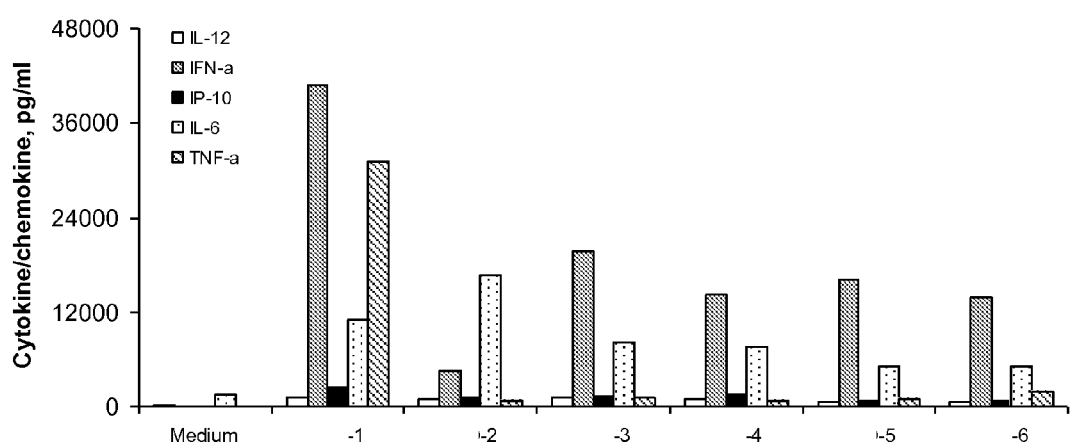
FIGS. 5A and 5B depict cytokine and chemokine concentrations from human plasmacytoid dendritic cells (pDCs) that were isolated, cultured, treated and analyzed according to Example 3 below. Briefly, the pDCs were isolated from freshly obtained healthy human volunteer's blood PBMCs and cultured with 10 μg/ml dose of immune modulatory oligonucleotides according to the invention for 24 hr. Supernatants were collected and analyzed by Luminex multiplex assay for cytokine and chemokine levels.
Figure 5B:
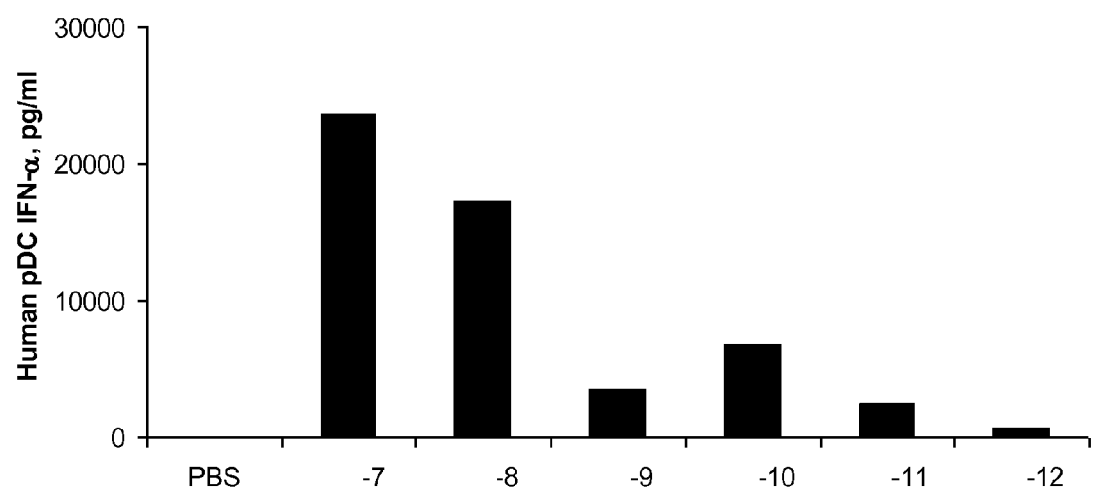
Figure 6A:
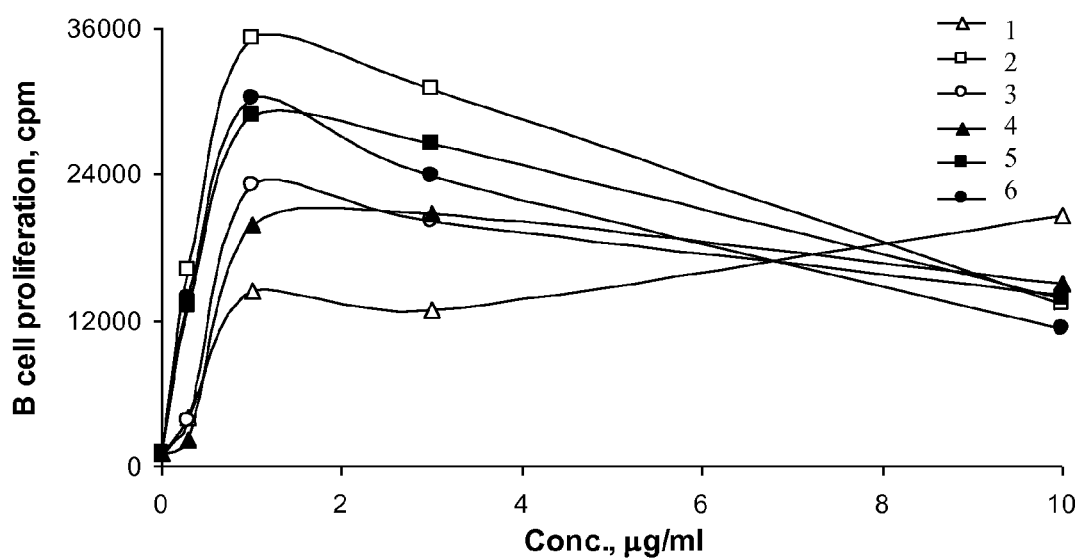
FIGS. 6A-6F depict human B-cell proliferation induced by immune modulatory oligonucleotides according to the invention. The human B-cells were isolated, cultured, treated and analyzed according to Example 4 below. Briefly, the Human B cells isolated from freshly obtained healthy human volunteer's PBMCs were cultured with different doses of immune modulatory oligonucleotides according to the invention for 68 hours and pulsed with $^3$H-thymidine for 6-8 hours. $^3$H-Thymidine uptake was determined using a liquid scintillation counter.
Figure 6B:
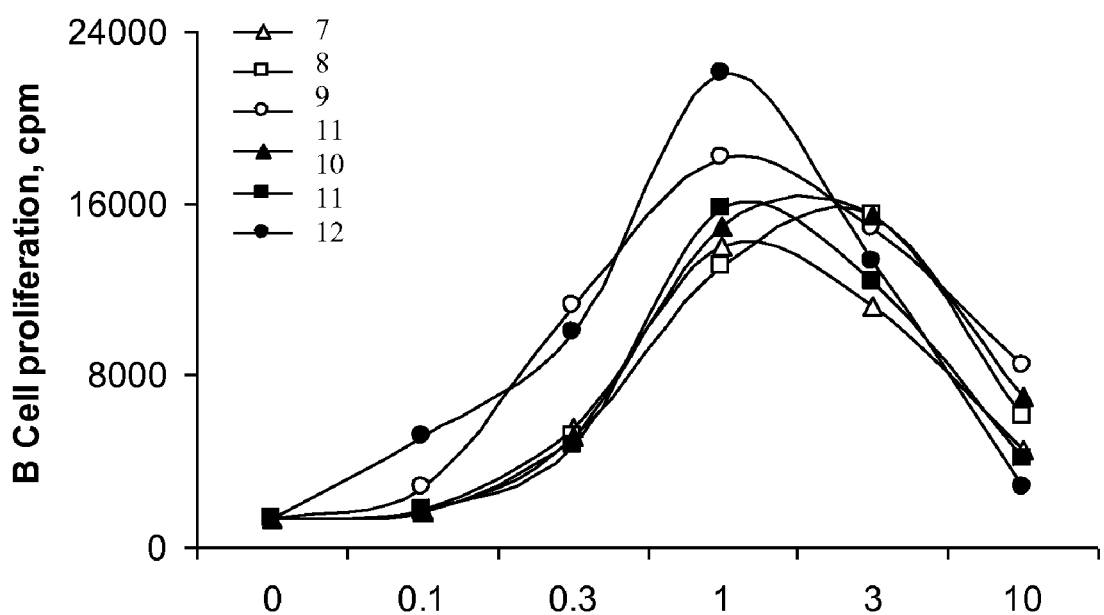
Figure 6C:
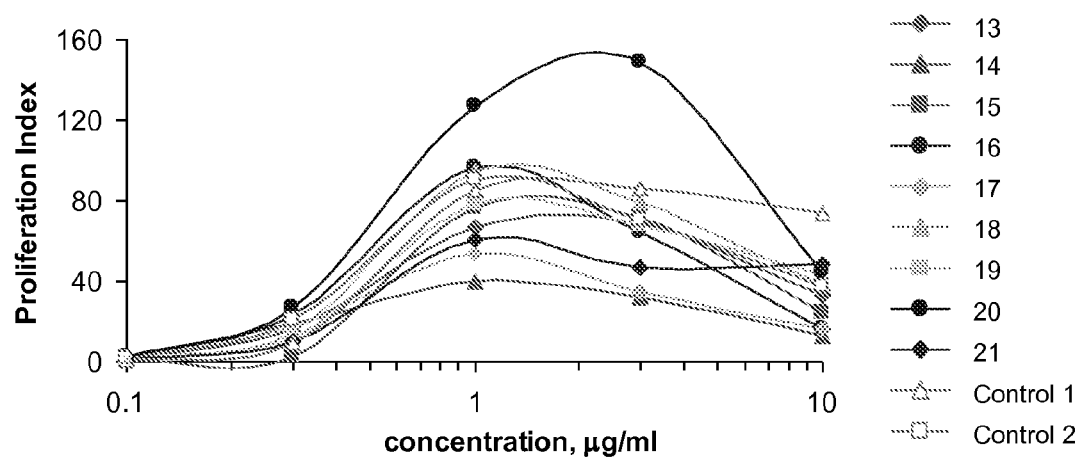
Figure 6D:
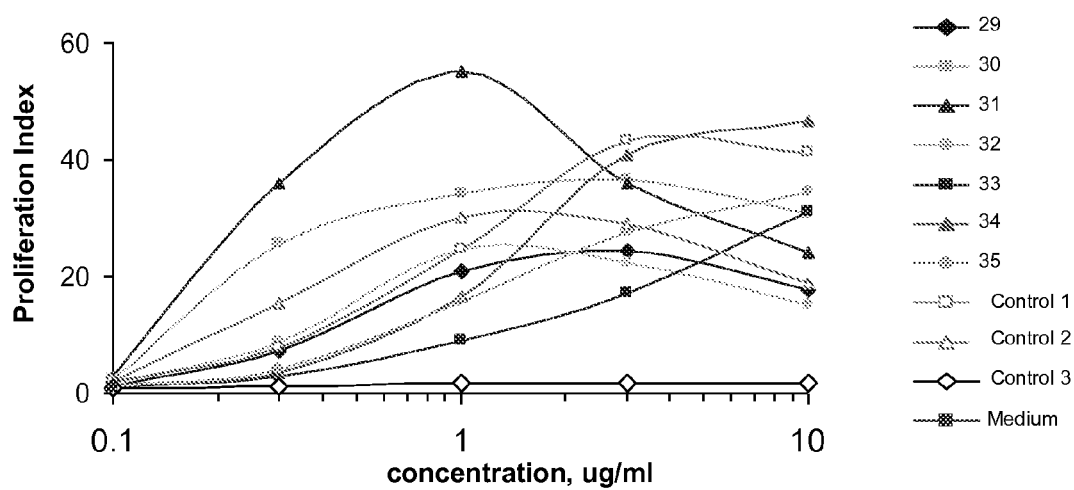
Figure 6E:
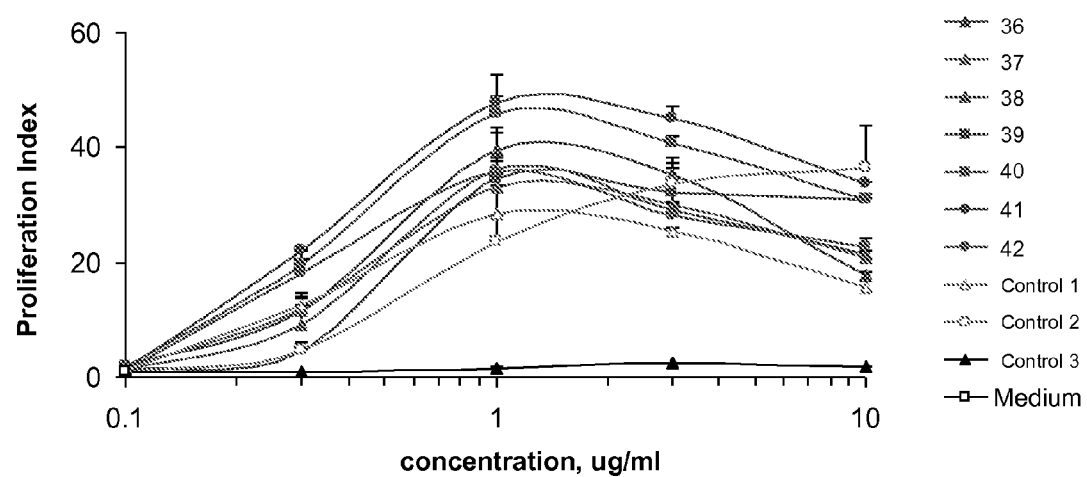
Figure 6F:
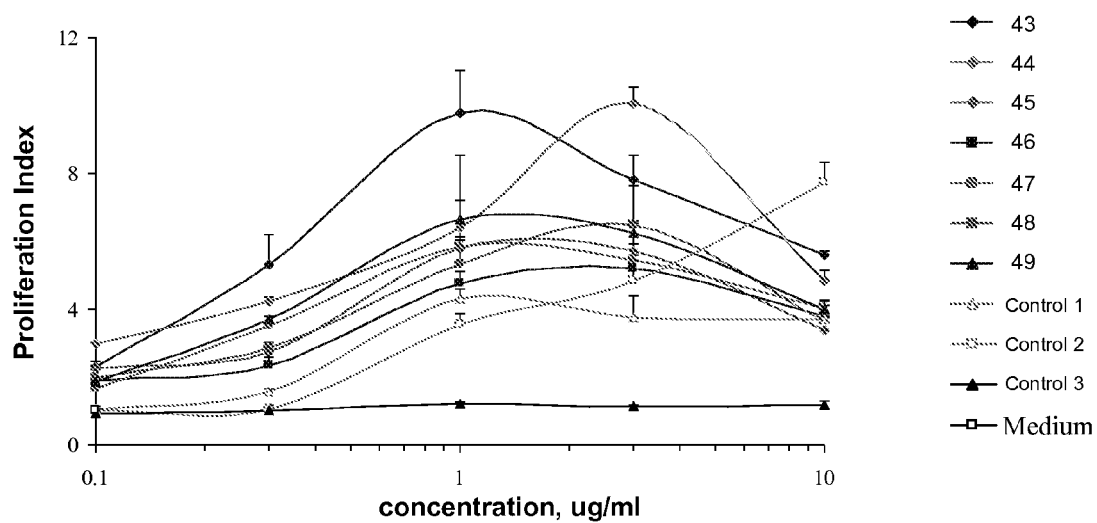
Figure 7A:
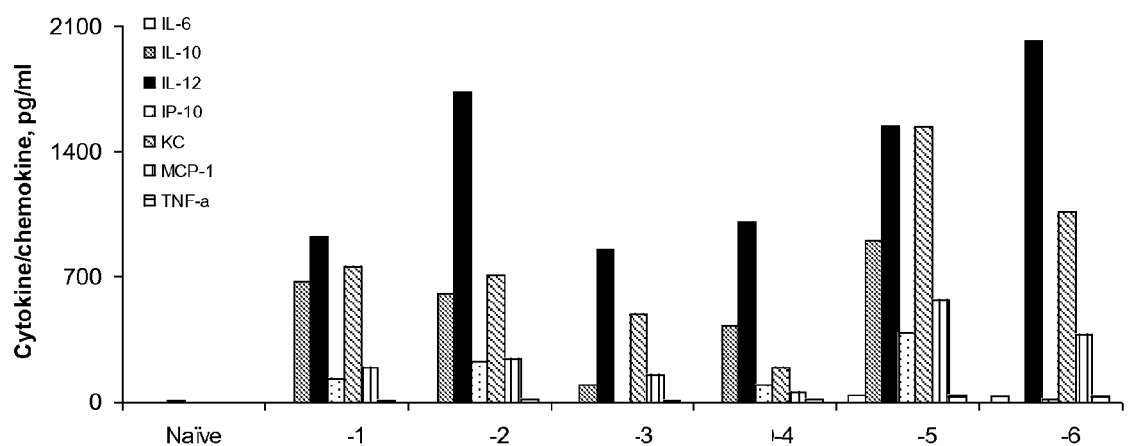
FIG. 7A depicts serum cytokine and chemokine induction in C57BL/6 mice that were treated according to Example 5 below. Briefly, 2 hours after the mice were injected subcutaneously with 1 mg/kg dose of immune modulatory oligonucleotides according to the invention, serum was collected and analyzed by Luminex multiplex assay for cytokine and chemokine levels.
Figure 7B:
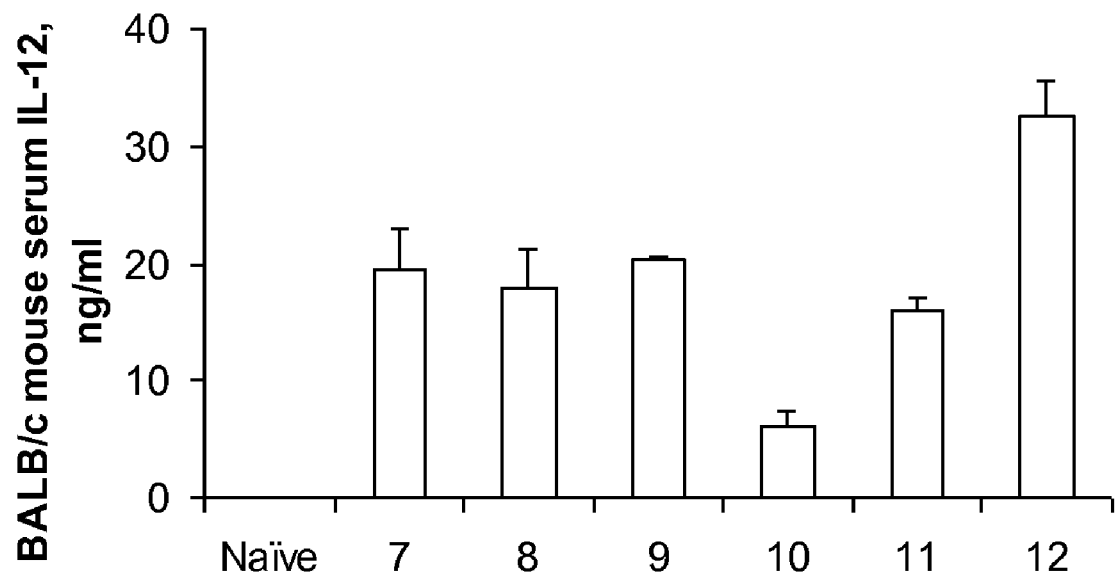
FIG. 7B depicts serum cytokine induction in BALB/c mice that were treated according to Example 5 below. Briefly, 2 hours after the mice were injected subcutaneously with 1 mg/kg dose of immune modulatory oligonucleotides according to the invention, serum was collected and analyzed by ELISA for IL-12 levels.
Figure 7C:
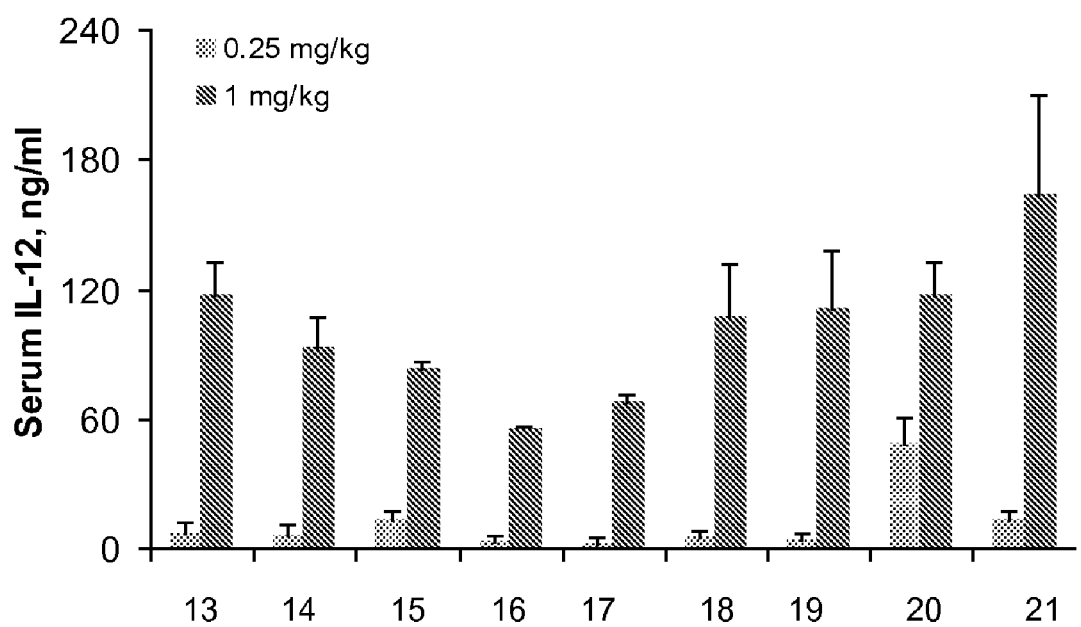
FIGS. 7C-7F depict serum cytokine induction in BALB/c mice that were treated according to Example 5 below. Briefly, 2 hours after the mice were injected subcutaneously with 0.25 or 1 mg/kg dose of immune modulatory oligonucleotides according to the invention, serum was collected and analyzed by ELISA for IL-12 levels.
Figure 7D:
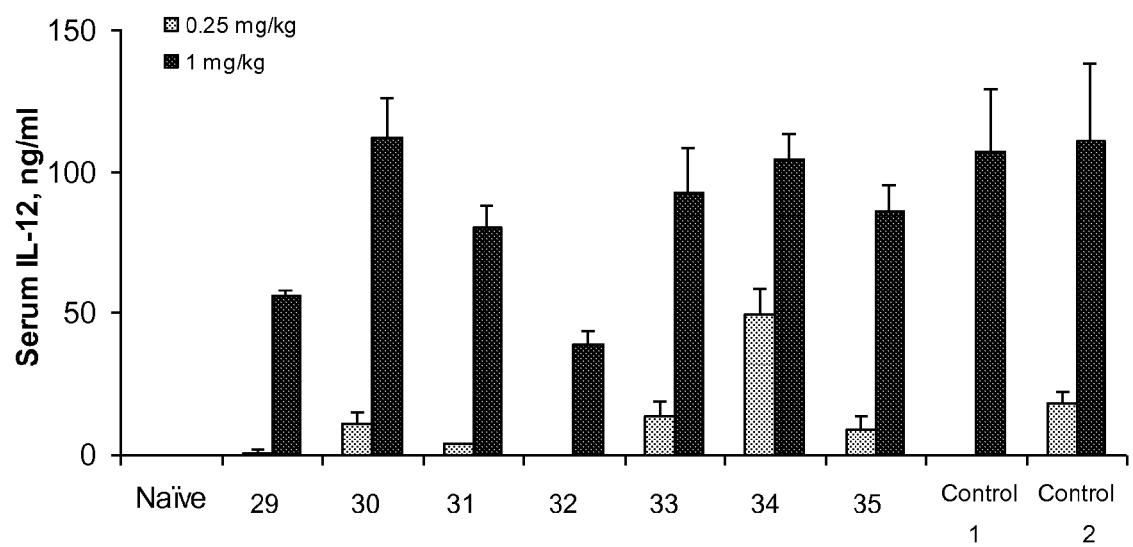
Figure 7E:
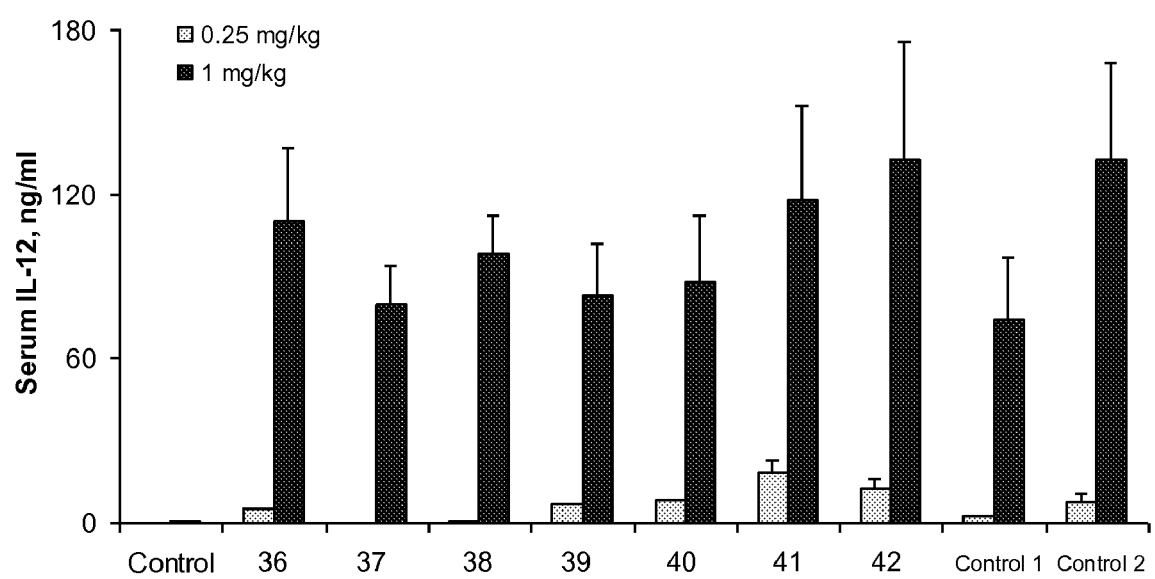
Figure 7F:
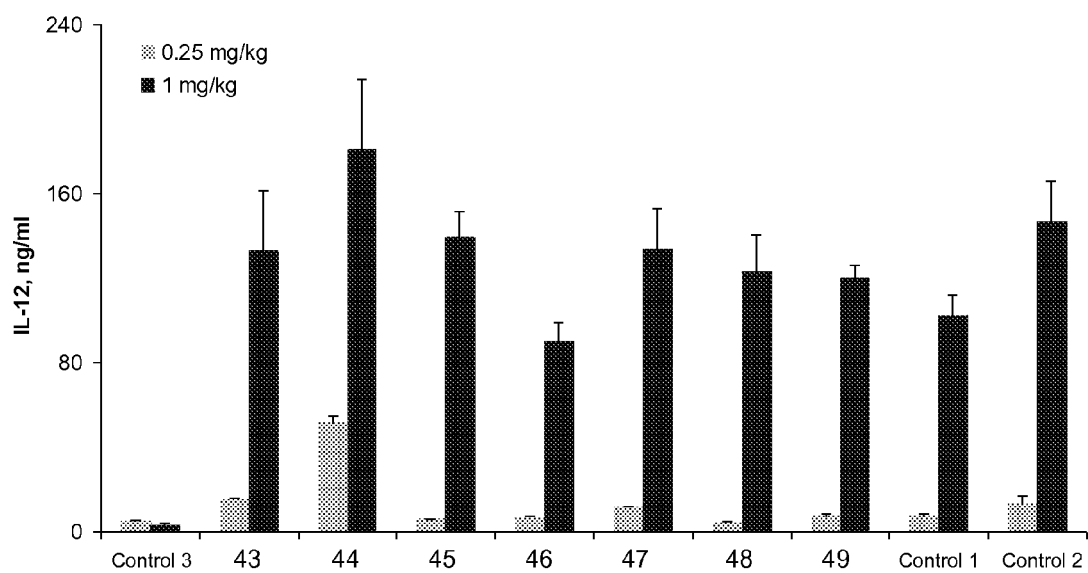

Exemplar TLR9 agonists from Table I were tested for immune stimulatory activity in the human pDC assays for IL-12, IL-6, IFN-α, IP-10, MIP-1α, MIP-1β, and TNFα, as described in Example 3. The results shown in FIGS. 5A and 5B demonstrate that specific chemical modifications to 3'-3' linked oligonucleotides will alter their TLR9 mediated immune activation profile in human pDCs. More generally, these data demonstrate that specific chemical modifications to 3'-3' linked oligonucleotides can be used to increase or decrease IL-12, IL-6, IFN-α, IP-10, MIP-1α, MIP-1β, and TNFα activation.

Exemplar TLR9 agonists from Table I were tested for immune stimulatory activity in the human B-cell proliferation assay, as described in Example 4. The results shown in FIGS. 6A, 6B, 6C, 6D, 6E and 6F demonstrate that specific chemical modifications to 3'-3' linked oligonucleotides will alter their TLR9 mediated B-cell proliferation activity and that this activation profile may be dose dependent depending on the chemical modification. More generally, these data demonstrate that specific chemical modifications to 3'-3' linked oligonucleotides can be used to regulate B-cell proliferation.

Exemplar TLR9 agonists from Table I were tested for in vivo immune stimulatory activity in C57Bl/6 and BALB/c mice, as described in Example 5. The results shown in FIGS. 7A, 7B, 7D, 7E and 8F demonstrate that specific chemical modifications to 3'-3' linked oligonucleotides will alter their in vivo TLR9 medicated immune activation profile in mouse models. More generally, these data demonstrate that specific chemical modifications to 3'-3' linked oligonucleotides can alter in vivo cytokine and/or chemokine concentrations, which will find application in many diseases.

As described above, the invention provides, in a first aspect, oligonucleotide-based synthetic agonists of TLR9. Based upon certain chemical modifications to the base, sugar, linkage or linker, the agonists of TLR9 may possess increased stability when associated and/or duplexed with other of the TLR9 agonist molecules, while retaining an accessible 5'-end.

In some embodiments, the non-nucleotidic linker may include, but are not limited to, those listed in Table II.

TABLE II

Representative Non-nucleotidic Linkers

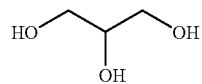

Glycerol (1,2,3-Propanetriol)

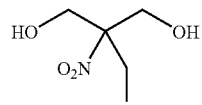

1,1,1-Tris(hydroxymethyl)nitromethane

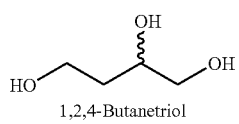

1,2,4-Butanetriol

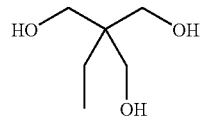

1,1,1-Tris(hydroxymethyl)propane

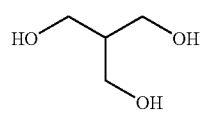

(2-hydroxymethyl)-1,3-propanediol

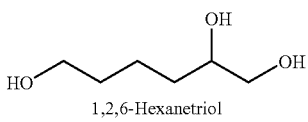

1,2,6-Hexanetriol

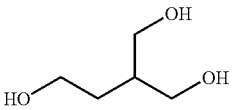

2-(hydroxymethyl)-1,4-butanediol

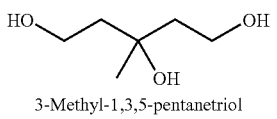

3-Methyl-1,3,5-pentanetriol

TABLE II-continued
Representative Non-nucleotidic Linkers
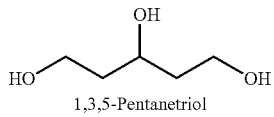
1,3,5-Pentanetriol
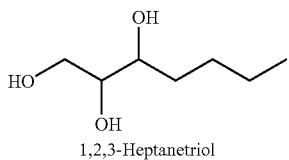
1,2,3-Heptanetriol
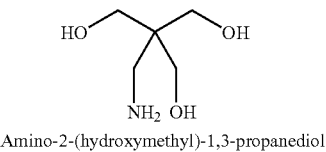
1,1,1-Tris(hydroxymethyl)ethane
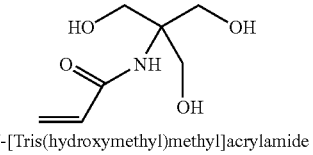
2-Amino-2-(hydroxymethyl)-1,3-propanediol
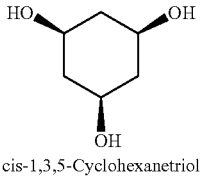
N-[Tris(hydroxymethyl)methyl]acrylamide
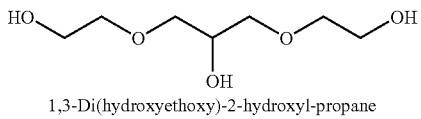
cis-1,3,5-Cyclohexanetriol
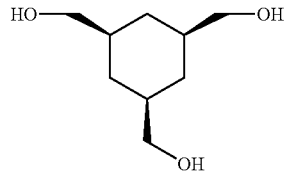
1,3-Di(hydroxyethoxy)-2-hydroxyl-propane
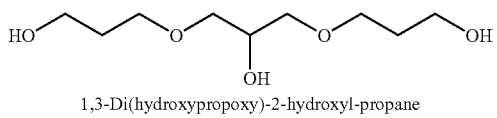
cis-1,3,5-Tri(hydroxymethyl)cyclohexane
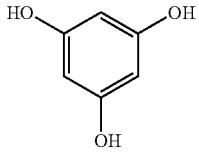
1,3-Di(hydroxypropoxy)-2-hydroxyl-propane
1,3,5,-Trihydroxyl-benzene TABLE II-continued
Representative Non-nucleotidic Linkers
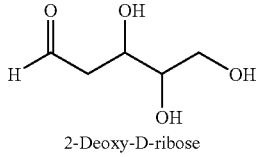
2-Deoxy-D-ribose
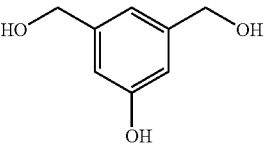
3,5,-Di(hydroxymethyl)phenol
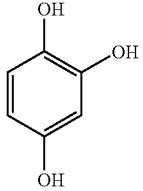
1,2,4,-Trihydroxyl-benzene
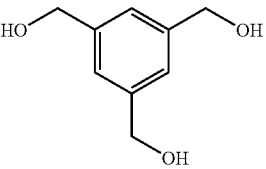
1,3,5,-Tri(hydroxymethyl)benzene
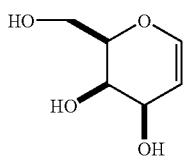
D-Galactoal
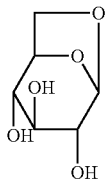
1,6-anhydro-β-D-Glucose
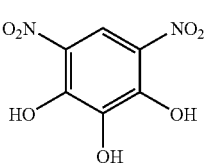
4,6-Nitropyrogallol
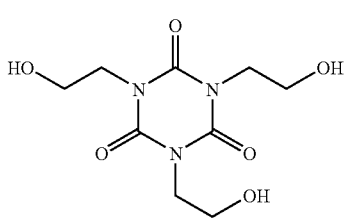
1,3,5-Tris(2-hydroxyethyl)-Cyanuric acid TABLE II-continued
Representative Non-nucleotidic Linkers
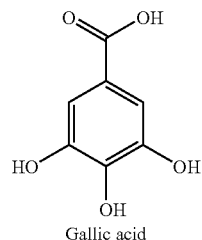
Gallic acid
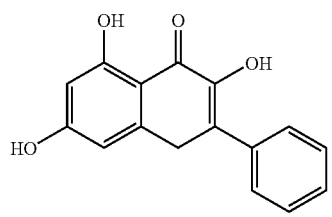
3,5,7-Trihydroxyflavone
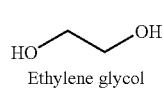
Ethylene glycol
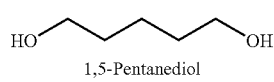
1,5-Pentanediol
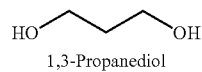
1,3-Propanediol
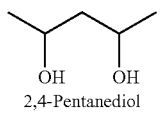
2,4-Pentanediol
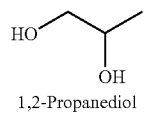
1,2-Propanediol
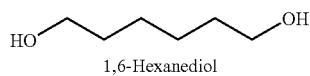
1,6-Hexanediol
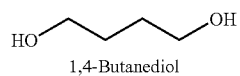
1,4-Butanediol
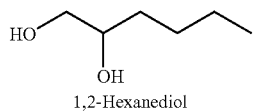
1,2-Hexanediol
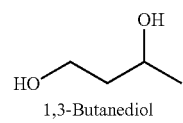
1,3-Butanediol
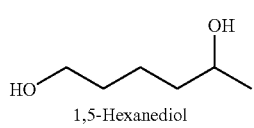
1,5-Hexanediol TABLE II-continued
Representative Non-nucleotidic Linkers
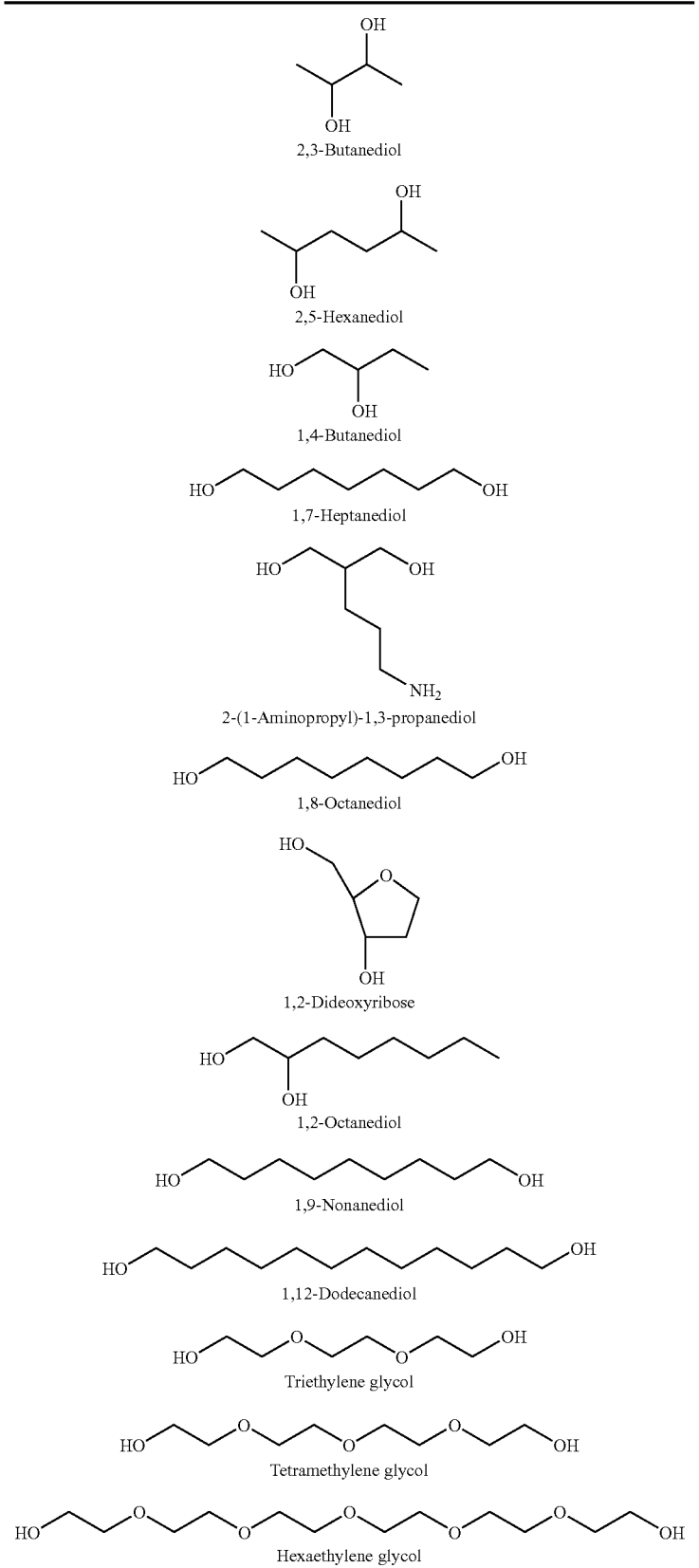

TABLE II-continued

Representative Non-nucleotidic Linkers

Cis, cis-cyclohexanetriol linker

Cis, trans-cyclohexanetriol linker 1,3,4-Isobutanetriol

Cyanuric Acid

---

In a second aspect, the invention provides pharmaceutical formulations comprising an oligonucleotide-based TLR9 agonist ("a compound") according to the invention and a pharmaceutically acceptable carrier.

The active compound is included in the pharmaceutically acceptable carrier or diluent in an amount sufficient to deliver to a patient a pharmaceutically effective amount without causing serious toxic effects in the patient treated. The effective dosage range of the pharmaceutically acceptable derivatives can be calculated based on the weight of the parent compound to be delivered, or by other means known to those skilled in the art. If the derivative exhibits activity in itself, the effective dosage can be estimated as above using the weight of the derivative, or by other means known to those skilled in the art.

In a third aspect, the invention provides a vaccine. Vaccines according to this aspect comprise a pharmaceutical formulation according to the invention, and further comprise an antigen. An antigen is a molecule that elicits a specific immune response. Such antigens include, without limitation, proteins, peptides, nucleic acids, carbohydrates and complexes or combinations of any of the same. Any such antigen may optionally be linked to an immunogenic protein or peptide, such as keyhole limpet hemocyanin (KLH), cholera toxin B subunit, or any other immunogenic carrier protein.

Vaccines according to the invention may further include any of the plethora of known adjuvants, including, without limitation, Freund's complete adjuvant, Keyhole Limpet Hemocyanin (KLH), monophosphoryl lipid A (MPL), alum, and saponins, including QS-21, imiquimod, R848, TLR agonists or combinations thereof.

In a fourth aspect, the invention provides methods for generating a TLR9-mediated immune response in an individual, such methods comprising administering to the individual a compound, pharmaceutical formulation or vaccine according to the invention. In some embodiments, the individual is a mammal. In preferred embodiments, the compound, pharmaceutical formulation or vaccine is administered to an individual in need of immune stimulation.

In the methods according to this aspect of the invention, administration of a compound, pharmaceutical formulation or vaccine according to the invention can be by any suitable route, including, without limitation, parenteral, oral, intratumoral, sublingual, transdermal, topical, intranasal, aerosol, intraocular, intratracheal, intrarectal, mucosal, vaginal, by gene gun, dermal patch or in eye drop or mouthwash form. Administration of the compound, pharmaceutical formulation or vaccine can be carried out using known procedures at dosages and for periods of time effective to reduce symptoms or surrogate markers of the disease. When administered systemically, the compound, pharmaceutical formulation or vaccine is preferably administered at a sufficient dosage to attain a blood level of a compound according to the invention from about 0.0001 micromolar to about 10 micromolar. For localized administration, much lower concentrations than this may be effective, and much higher concentrations may be tolerated without serious toxic effects. Preferably, a total dosage of a compound according to the invention ranges from about 0.001 mg per patient per day to about 200 mg per kg body weight per day. It may be desirable to administer simultaneously, or sequentially a therapeutically effective amount of one or more of the therapeutic compositions of the invention to an individual as a single treatment episode.

In certain preferred embodiments, a compound, pharmaceutical formulation or vaccine according to the invention is co-administered or administered in combination with another agent, including without limitation antibodies, cytotoxic agents, allergens, antibiotics, antisense oligonucleotides, siRNA, aptamers, ribozymes, targeted therapies, kinase inhibitors, peptides, proteins, gene therapy vectors, DNA vaccines, and/or adjuvants to enhance the specificity or magnitude of the immune response.

The methods according to this aspect of the invention are useful for the prophylactic or therapeutic treatment of human or animal disease. For example, the methods are useful for pediatric and veterinary vaccine applications. The methods are also useful for model studies of the immune system.

In a fifth aspect, the invention provides methods for therapeutically treating a patient having a disease or disorder, such methods comprising administering to the patient a compound, pharmaceutical formulation or vaccine according to the invention. In various embodiments, the disease or disorder to be treated is cancer, an autoimmune disorder, infectious disease, airway inflammation, inflammatory disorders, allergy, asthma or a disease caused by a pathogen or allergen. Pathogens include for example bacteria, parasites, fungi, viruses, viroids, and prions. Administration is carried out as described for the fourth aspect of the invention.

In a sixth aspect, the invention provides methods for preventing a disease or disorder, such methods comprising administering to the patient a compound, pharmaceutical formulation or vaccine according to the invention. In various embodiments, the disease or disorder to be prevented is cancer, an autoimmune disorder, airway inflammation, inflammatory disorders, infectious disease, allergy, asthma or a disease caused by a pathogen. Pathogens include, without limitation, bacteria, parasites, fungi, viruses, viroids, and prions. Administration is carried out as described for the fourth aspect of the invention.

In any of the methods according to the invention, the compound, pharmaceutical formulation or vaccine according to the invention can be co-administered or administered in combination with any other agent useful for preventing or treating the disease or condition that does not abolish the immune stimulatory effect of the compound, pharmaceutical formulation or vaccine according to the invention. In any of the methods according to the invention, the agent useful for preventing or treating the disease or condition includes, but is not limited to, vaccines, antigens, antibodies, cytotoxic agents, allergens, antibiotics, antisense oligonucleotides, TLR agonists, kinase inhibitors, peptides, proteins, gene therapy vectors, DNA vaccines and/or adjuvants to enhance the specificity or magnitude of the immune response, or co-stimulatory molecules such as cytokines, chemokines, protein ligands, trans-activating factors, peptides and peptides comprising modified amino acids. For example, in the prevention and/or treatment of cancer, it is contemplated that the compound, pharmaceutical formulation or vaccine according to the invention may be co-administered or administered in combination with a chemotherapeutic compound or a monoclonal antibody. Preferred chemotherapeutic agents include, without limitation Gemcitabine methotrexate, vincristine, adriamycin, cisplatin, non-sugar containing chloroethylnitrosoureas, 5-fluorouracil, mitomycin C, bleomycin, doxorubicin, dacarbazine, Taxol®, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone®/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, imatinib mesylate/Gleevec®, Picibanil/OK-432, AD 32/Valrubicin, Metastron®/strontium derivative, Temodal/Temozolomide, Evacet/liposomal doxorubicin, Yewtaxan/Placlitaxel, Taxol®/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT™ (Tegafur/Uracil), Ergamisol®/Levamisole, Eniluracil/776C85/5FU enhancer, Campto/Levamisole, Camptosar®/Irinotecan, Tumodex/Ralitrexed, Leustatin®/Cladribine, Paxex/Paclitaxel, Doxil®/liposomal doxorubicin, Caelyx/liposomal doxorubicin, Fludara®/Fludarabine, Pharmarubicin/Epirubicin, DepoCyt®, ZD1839, LU 79553/Bis-Naphtalimide, LU 103793/Dolastain, Caetyx/liposomal doxorubicin, Gemzar®/Gemcitabine, ZD 0473/Anormed®, YM 116, Iodine seeds, CDK4 and CDK2 inhibitors, PARP inhibitors, D4809/Dexifosamide, Ifes/Mesnex®/Ifosamide, Vumon®/Teniposide, Paraplatin®/Carboplatin, Plantinol/cisplatin, Vepeside/Etoposide, ZD 9331, Taxotere®/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate. Preferred monocloncal antibodies include, but are not limited to, Panorex® (Glaxo-Welicome), Rituxan® (IDEC/Genentech/Hoffman la Roche), Mylotarg® (Wyeth), Campath® (Millennium), Zevalin® (IDEC and Schering AG), Bexxar® (Corixa/GSK), Erbitux® (Imclone/BMS), Avastin® (Genentech) Herceptin® (Genentech/Hoffman la Roche), Tarceva® (OSI Pharmaceuticals/Genentech).

Alternatively, the agent useful for preventing or treating the disease or condition can include DNA vectors encoding for antigen or allergen. In these embodiments, the compound, pharmaceutical formulation or vaccine according to the invention can variously act as adjuvants and/or produce direct immunomodulatory effects.

The following examples are intended to further illustrate certain preferred embodiments of the invention and are not intended to limit the scope of the invention in any way.

Example 1

Figure 2:
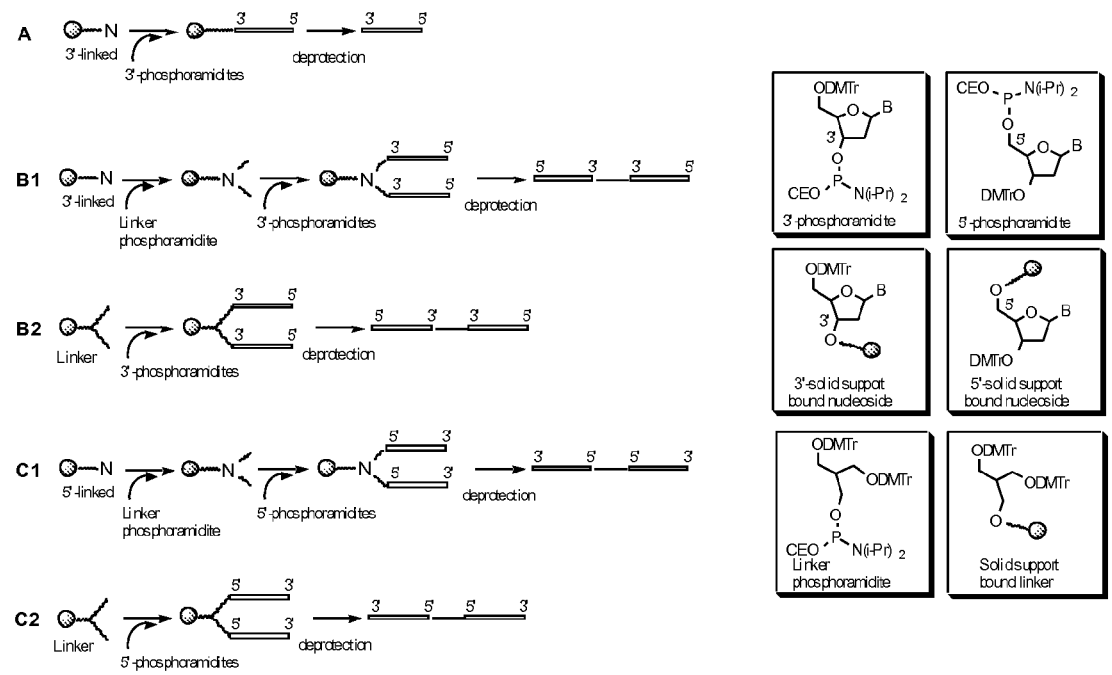
FIG. 2 is a synthetic scheme for the parallel synthesis of immune modulatory compound of the invention. DMTr=4,4'-dimethoxytrityl; CE=cyanoethyl.
Figure 3A:
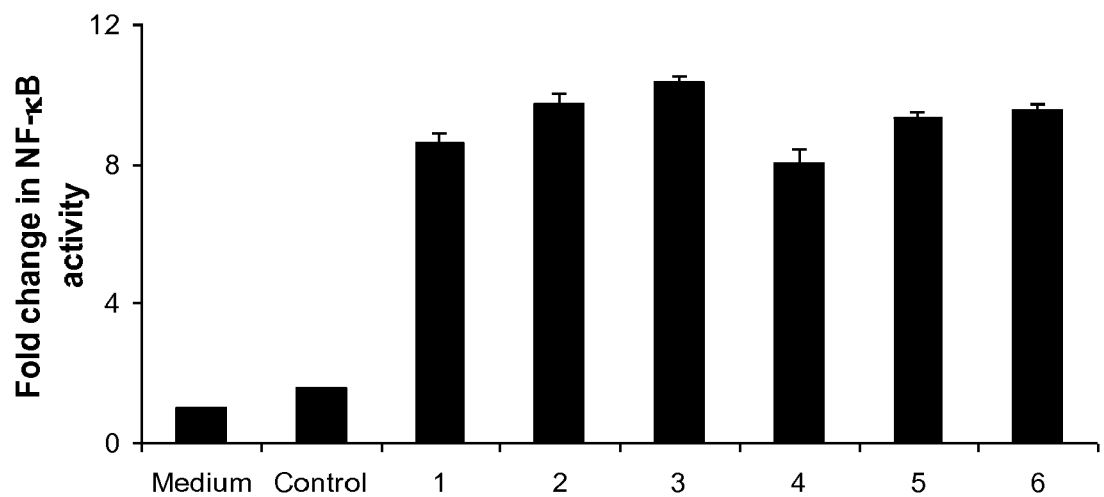
FIGS. 3A-3C depict NF-kB activity in HEK293 cells expressing TLR9 that were cultured, treated and analyzed according to Example 2 below. Briefly, the HEK293 cells were stimulated with 10 μg/ml of immune modulatory oligonucleotides according to the invention for 18 hours, and the levels of NF-κB were determined using SEAP (secreted form of human embryonic alkaline phosphatase) assay.
Figure 3B:
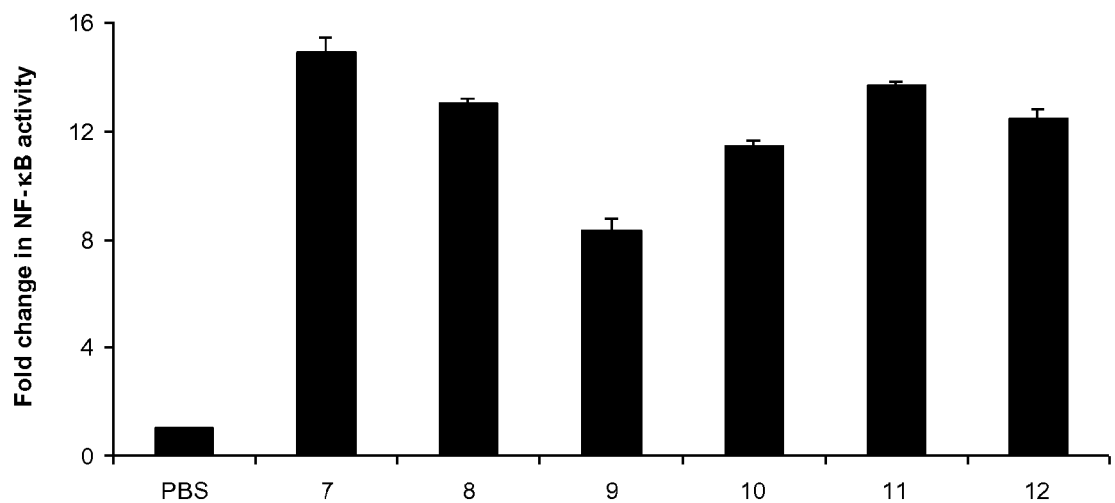
Figure 3C:
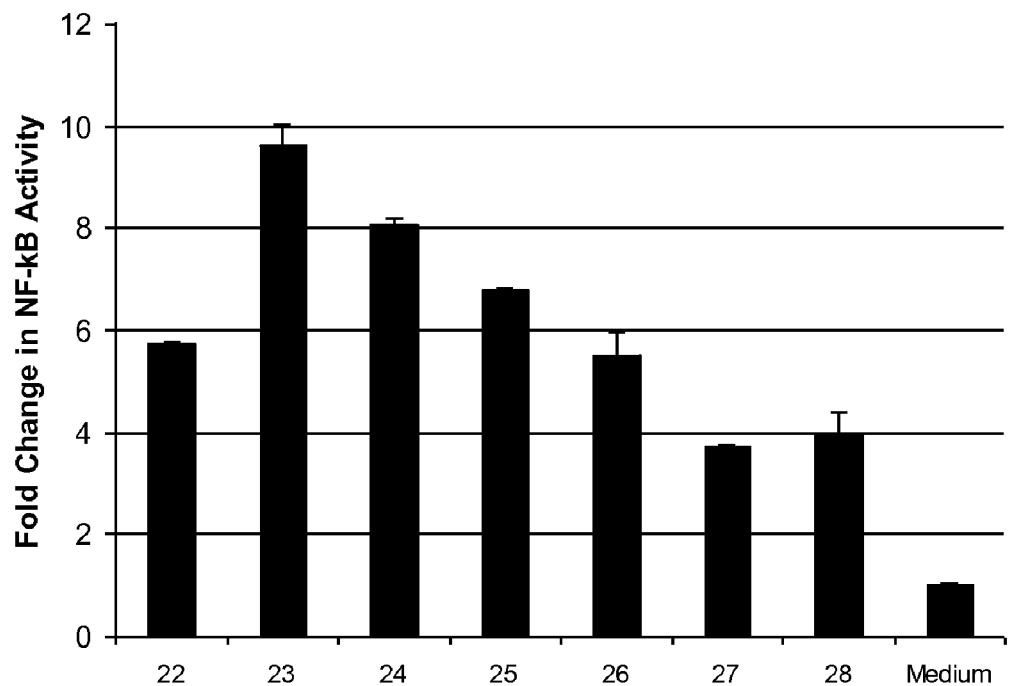
Figure 3D:
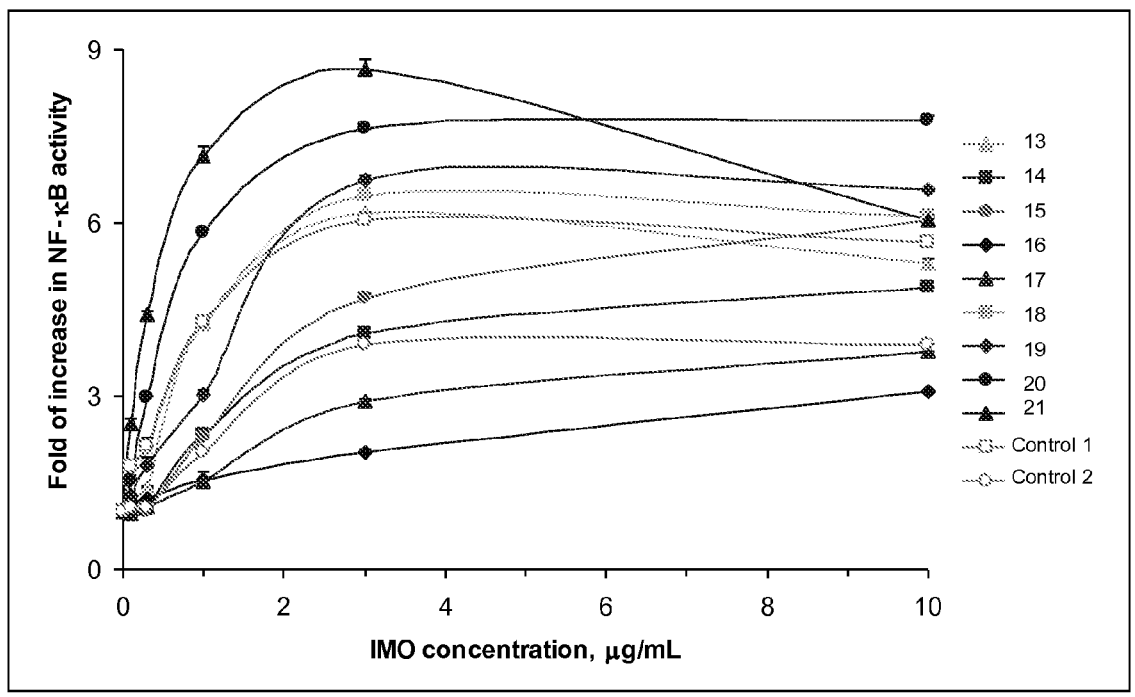
FIGS. 3D-3G depicts NF-kB activity in HEK293 cells expressing TLR9 that were cultured, treated and analyzed according to Example 2 below. Briefly, the HEK293 cells were stimulated with 0 (PBS/Media), 0.1, 0.3, 1.0, 3.0, or 10.0 μg/ml of immune modulatory oligonucleotides according to the invention for 18 hours, and the levels of NF-κB were determined using SEAP (secreted form of human embryonic alkaline phosphatase) assay.
Figure 3E:
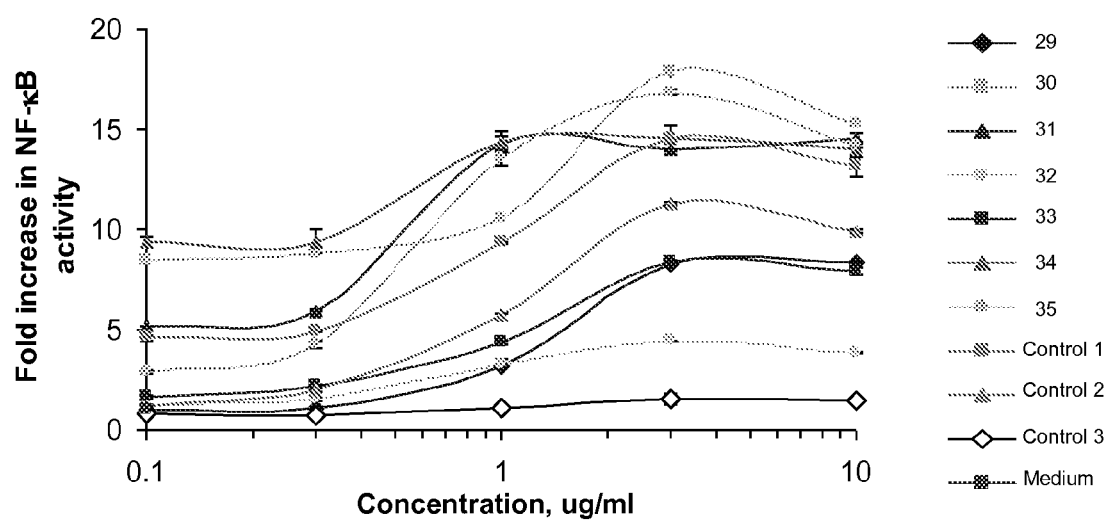
Figure 3F:
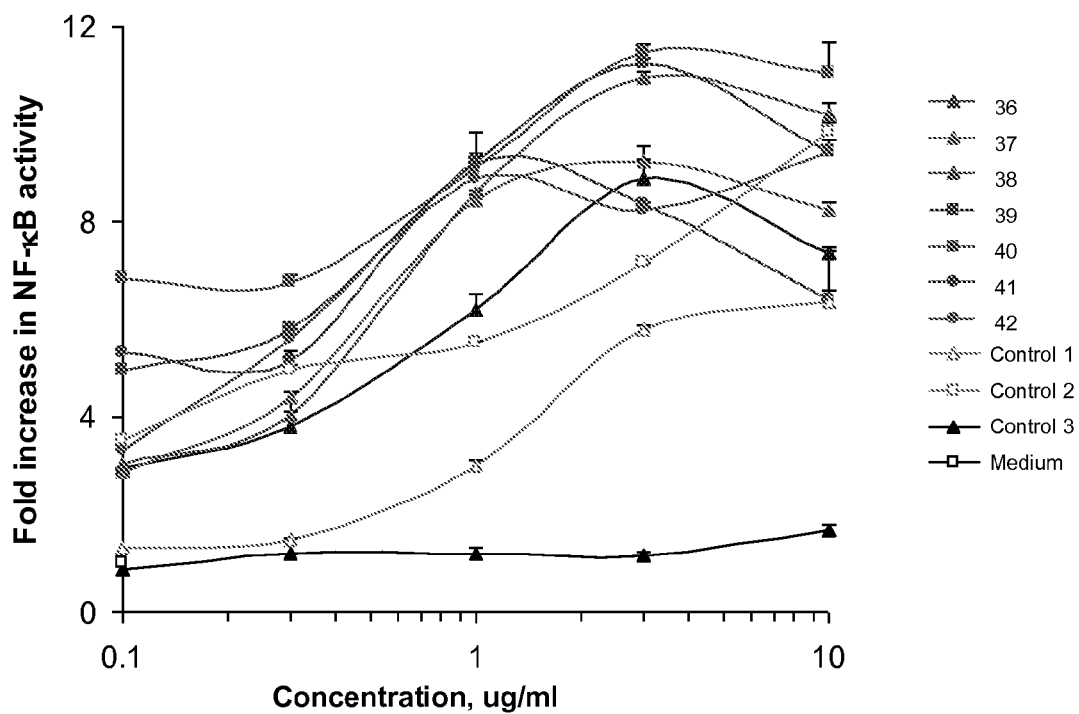
Figure 3G:
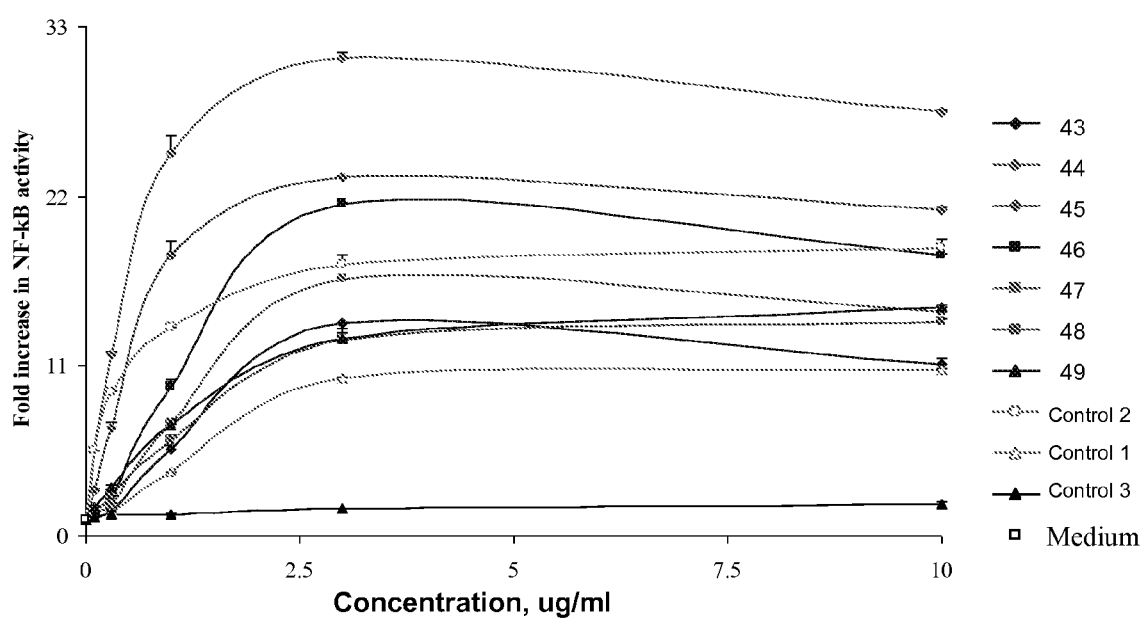
Figure 4A:
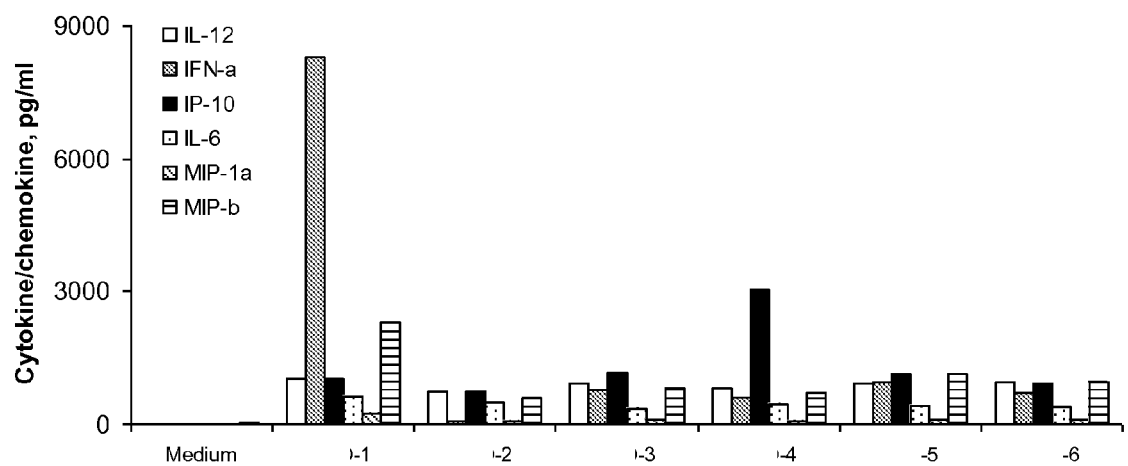
FIGS. 4A and 4B depict cytokine and chemokine concentrations from human PBMCs that were isolated, cultured, treated and analyzed according to Example 3 below. Briefly, the PBMCs were isolated from freshly obtained healthy human volunteer's blood and cultured with 10 μg/ml dose of immune modulatory oligonucleotides according to the invention for 24 hr. Supernatants were collected and analyzed by Luminex multiplex assay cytokine and chemokine levels.
Figure 4B:
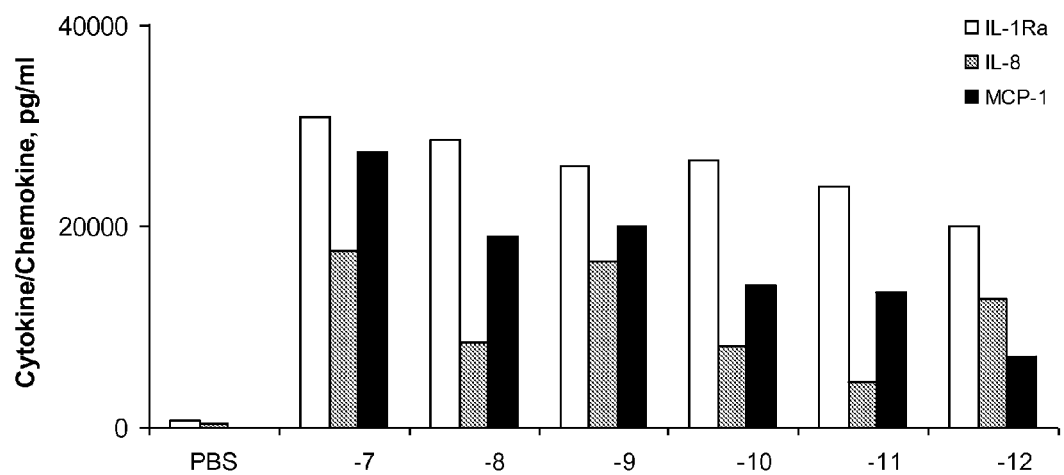
Figures 4C, 4D, 4E, 4F, 4G, 4H:
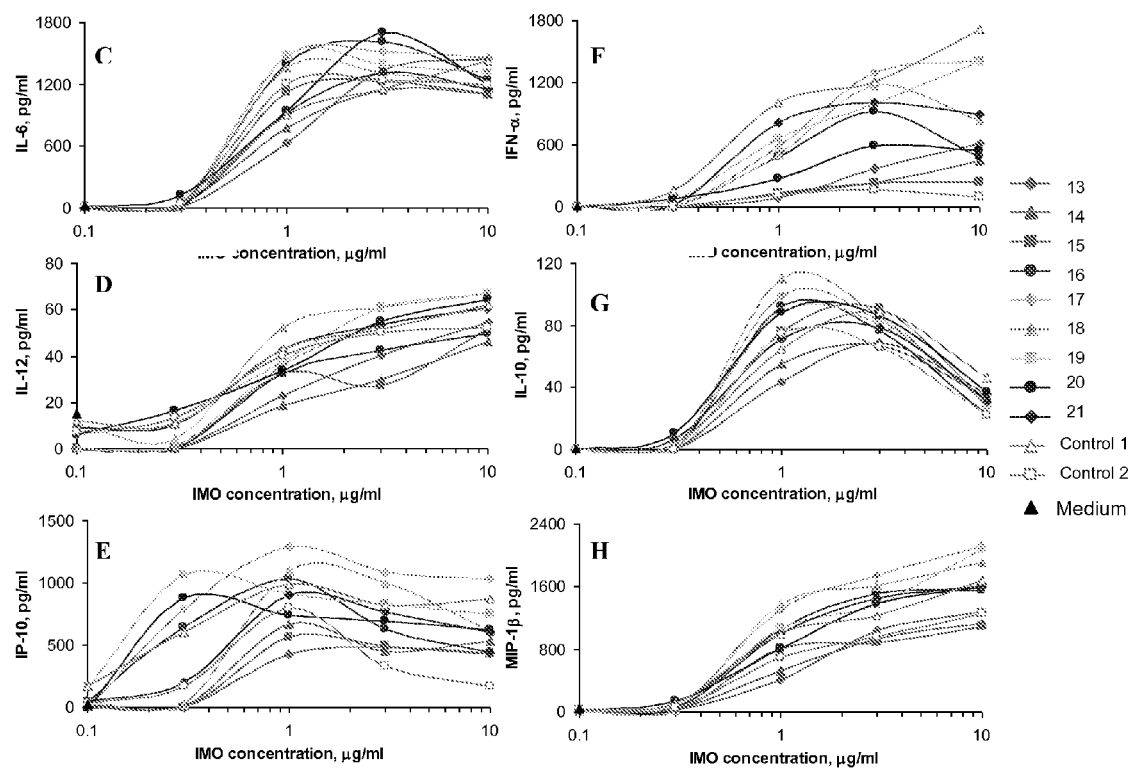
FIGS. 4C-4H depict cytokine and chemokine concentrations from human PBMCs that were isolated, cultured, treated and analyzed according to Example 3 below. Briefly, the PBMCs were isolated from freshly obtained healthy human volunteer's blood and cultured with 0 (PBS), 0.1, 0.3, 1.0, 3.0, or 10.0 μg/ml dose of immune modulatory oligonucleotides according to the invention for 24 hours. Supernatants were collected and analyzed by Luminex multiplex assay for cytokine and chemokine levels.
Figures 4O, 4P, 4Q, 4R, 4S, 4T:
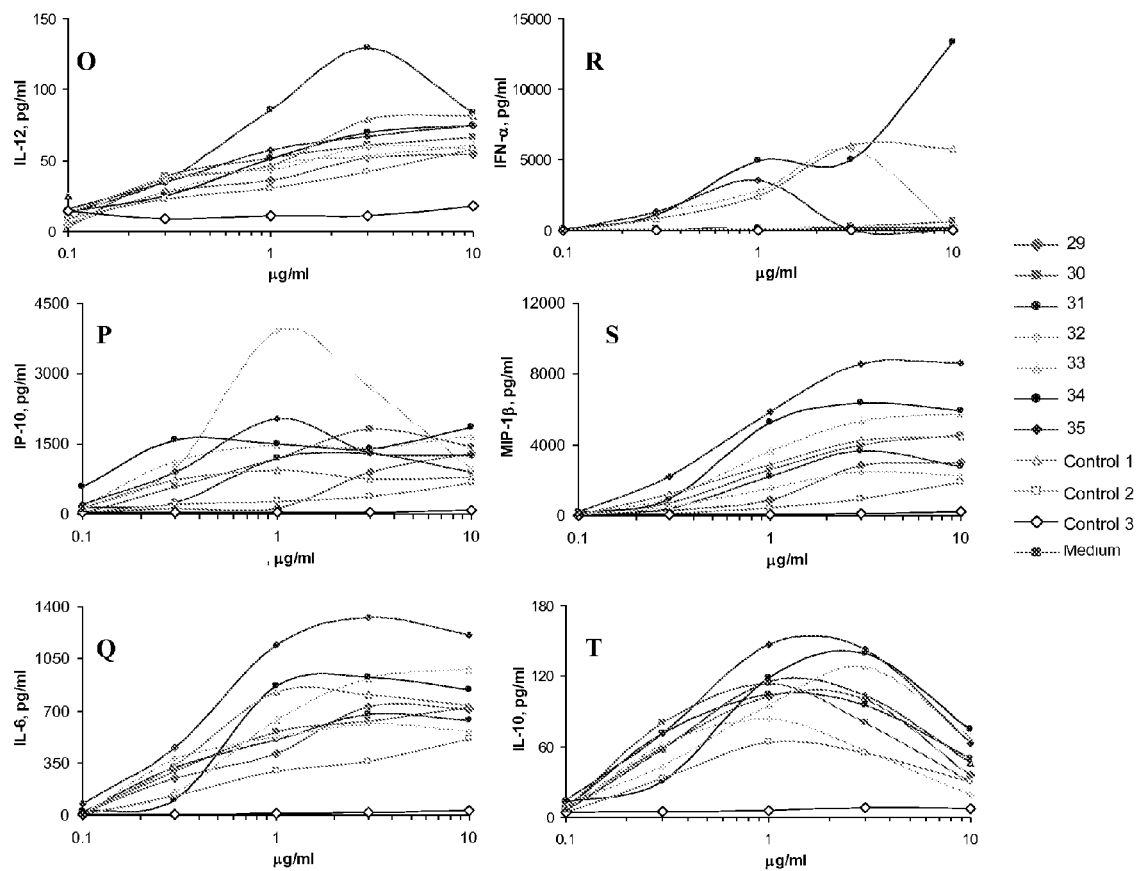
Figures 4U, 4V, 4W, 4X, 4Y, 4Z:
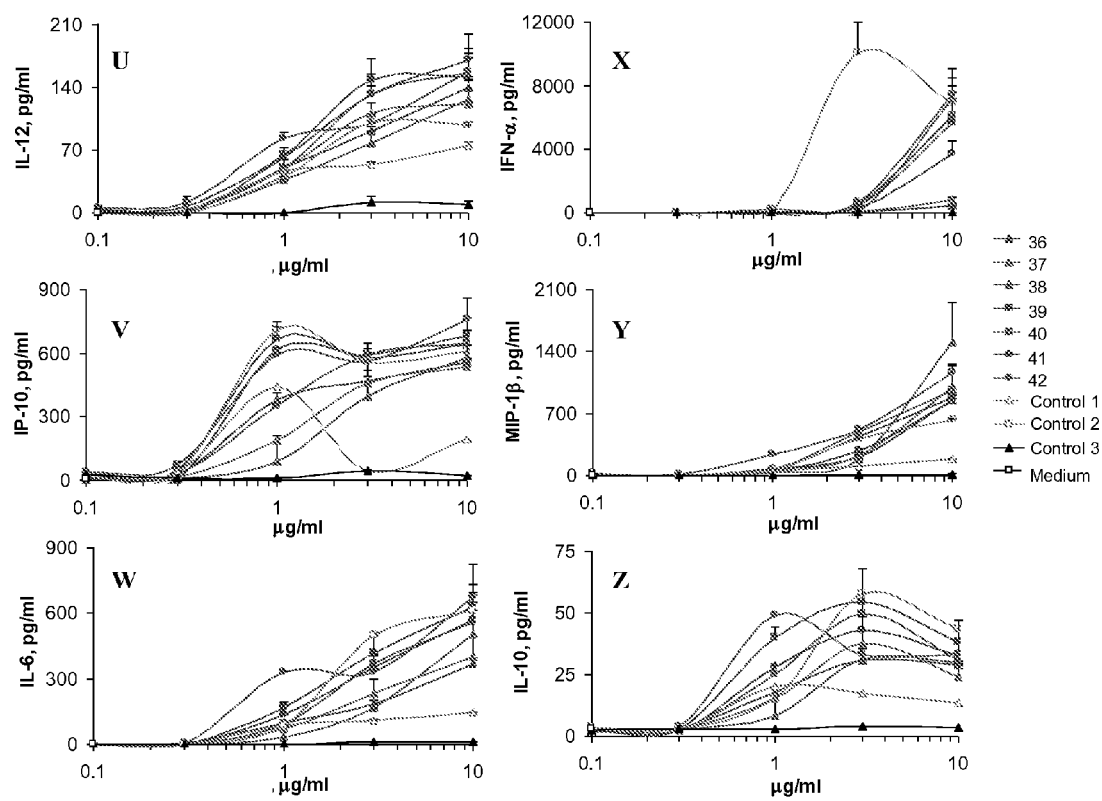
Figure 4A:
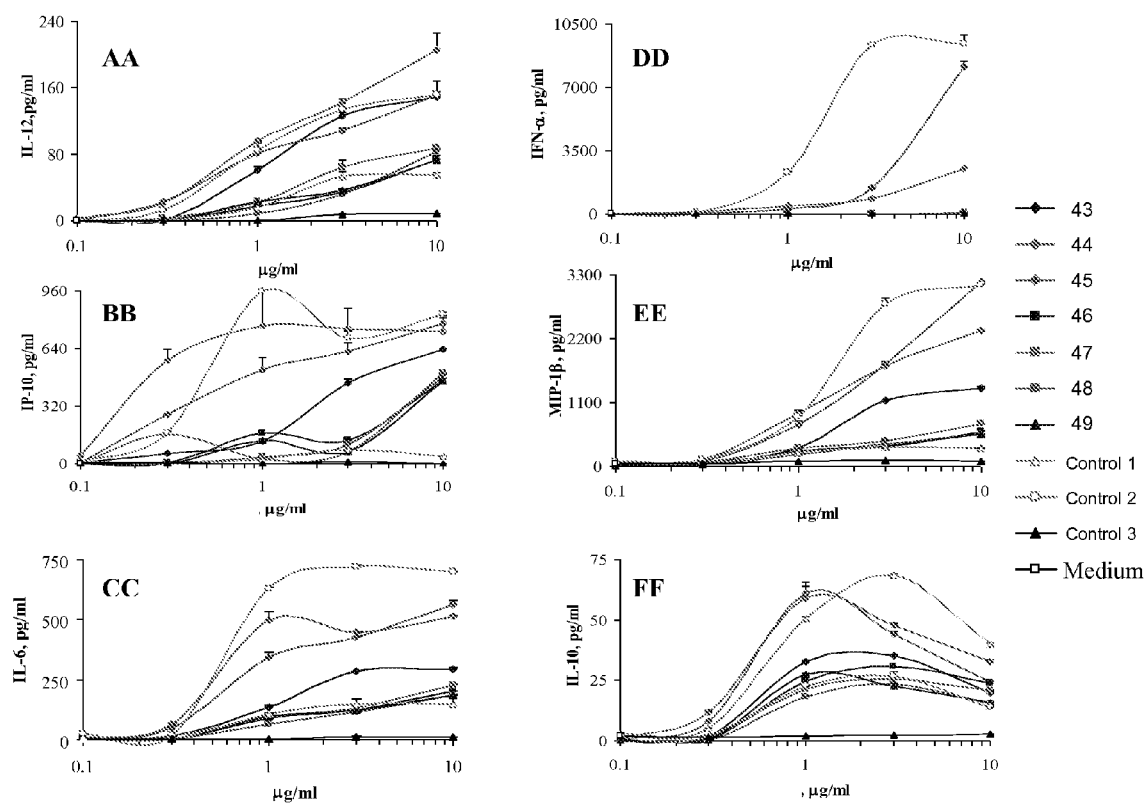

Synthesis of Oligonucleotide-Based Compounds Containing Immune Stimulatory Moieties Chemical entities according to the invention were synthesized on a 1 µmol to 0.1 mM scale using an automated DNA synthesizer (OligoPilot II, AKTA, (Amersham) and/or Expedite 8909 (Applied Biosystem)), following the linear synthesis or parallel synthesis procedures outlined in FIGS. 1 and 2.

5'-DMT dA, dG, dC and T phosphoramidites were purchased from Proligo (Boulder, Colo.). 5'-DMT 7-deaza-dG and araG phosphoramidites were obtained from Chemgenes (Wilmington, Mass.). DiDMT-glycerol linker solid support was obtained from Chemgenes. 1-(2'-deoxy-β-D-ribofuranosyl)-2-oxo-7-deaza-8-methyl-purine amidite was obtained from Glen Research (Sterling, Va.), 2'-O-methylribonunucleoside amidites were obtained from Promega (Obispo, Calif.). All compounds according to the invention were phosphorothioate backbone modified.

All nucleoside phosphoramidites were characterized by $^{31}$p and $^{1}$H NMR spectra. Modified nucleosides were incorporated at specific sites using normal coupling cycles recommended by the supplier. After synthesis, compounds were deprotected using concentrated ammonium hydroxide and purified by reverse phase HPLC, detritylation, followed by dialysis. Purified compounds as sodium salt form were lyophilized prior to use. Purity was tested by CGE and MALDI-TOF MS. Endotoxin levels were determined by LAL test and were below 1.0 EU/mg.

Example 2

Cell Culture Conditions and Reagents

HEK293 or HEK293XL cells expressing mouse TLR9 (Invivogen, San Diego, Calif.) were cultured in 48-well plates in 250 µl/well DMEM supplemented with 10% heat-inactivated FBS in a 5% $CO_2$ incubator. At 80% confluence, cultures were transiently transfected with 400 ng/ml of SEAP (secreted form of human embryonic alkaline phosphatase) reporter plasmid (pNifty2-Seap) (Invivogen) in the presence of 4 µl/ml of lipofectamine (Invitrogen, Carlsbad, Calif.) in culture medium. Plasmid DNA and lipofectamine were diluted separately in serum-free medium and incubated at room temperature for 5 minutes. After incubation, the diluted DNA and lipofectamine were mixed and the mixtures were incubated at room temperature for 20 minutes. Aliquots of 25 µl of the DNA/lipofectamine mixture containing 100 ng of plasmid DNA and 1 µl of lipofectamine were added to each well of the cell culture plate, and the cultures were continued for 4 hours.

Cytokine Induction by Exemplar Compounds from Table I in HEK293 Cells Expressing Mouse TLR9

After transfection, medium was replaced with fresh culture medium, exemplar compounds from Table I were added to the cultures at concentrations of 0, 0.1, 0.3, 1.0, 3.0, or 10.0 µg/ml, and the cultures were continued for 18 hours. At the end of compounds treatment, the levels of NF-κB were determined using SEAP (secreted form of human embryonic alkaline phosphatase) assay according to the manufacturer's protocol (Invivogen). Briefly, 30 µl of culture supernatant was taken from each treatment and incubated with p-nitrophynyl phosphate substrate and the yellow color generated was measured by a plate reader at 405 nm (Putta M R et al, Nucleic Acids Res., 2006, 34:3231-8).

Example 3

Cytokine Induction by Exemplar Compounds from Table I in Human PBMCs, pDCs, and Mouse Splenocytes Human PBMC Isolation
Peripheral blood mononuclear cells (PBMCs) from freshly drawn healthy volunteer blood (CBR Laboratories, Boston, Mass.) were isolated by Ficoll density gradient centrifugation method (Histopaque-1077, Sigma).
Human pDC Isolation
Human plasmacytoid dendritic cells (pDCs) were isolated from freshly obtained healthy human volunteer's blood PBMCs by positive selection using the BDCA4 cell isolation kits (Miltenyi Biotec) according to the manufacturer's instructions.
Mouse Splenocyte Isolation
Human PBMCs were plated in 48-well plates using $5 \times 10^6$ cells/ml. Human pDCs were plated in 96-well dishes using $1 \times 10^6$ cells/ml. The exemplar compounds from Table I dissolved in DPBS (pH 7.4; Mediatech) were added to the cell cultures at doses of 0, 0.1, 0.3, 1.0, 3.0, or 10.0 µg/ml. The cells were then incubated at 37° C. for 24 hours and the supernatants were collected for luminex multiplex or ELISA assays. In certain experiments, the levels of IFN-α, IL-6, and/or IL-12 were measured by sandwich ELISA. The required reagents, including cytokine antibodies and standards, were purchased from PharMingen.
Cytokine Luminex Multiplex
In certain experiments, the levels of IL-1Rα, IL-6, IL-10, IL-12, IFN-α, IFN-γ, MIP-1α, MIP-β, MCP-1, and IL-12p40p70 in culture supernatants were measured by Luminex multiplex assays, which were performed using Biosource human multiplex cytokine assay kits on Luminex 100 instrument and the data were analyzed using StarStation software supplied by Applied Cytometry Systems (Sacramento, Calif.).
Activation of Human Immune Cells
Human plasmacytoid dendritic cells (pDCs) were isolated from freshly obtained healthy human blood PBMCs and cultured with 50 µg/ml of TLR9 agonists or control for 24 hr. Cells were stained with fluorescently-conjugated Abs (CD123, CD80, CD86) and data were collected on an FC500 MPL cytometer. Mean fluorescence intensity of CD80 and CD86 on CD123$^+$ cells was analyzed using FlowJo software and is expressed as fold change over PBS control.
Human myeloid dendritic cells (mDC) were isolated from freshly obtained healthy human blood PBMCs and cultured with 50 µg/ml of TLR9 agonists or control for 24 hr. Cells were stained with fluorescently-conjugated Abs (CD11c, CD80, CD40) and data were collected on an FC500 MPL cytometer. Mean fluorescence intensity of CD80 and CD40 on CD11c$^+$ cells was analyzed using FlowJo software and is expressed as fold change over PBS control.

Example 4

Human B Cell Proliferation Assay in the Presence of Exemplar Compounds from Table I Human B cells were isolated from PBMCs by positive selection using the CD19 Cell Isolation Kit (Miltenyi Biotec, Auburn, Calif.) according to the manufacturer's instructions.

The culture medium used for the assay consisted of RPMI 1640 medium supplemented with 1.5 mM glutamine, 1 mM sodium pyruvate, 0.1 mM non-essential amino acids, 50 μM 2-mercaptoethanol, 100 IU/ml penicillin-streptomycin mix and 10% heat-inactivated fetal bovine serum.

A total of $0.5 \times 10^6$ B cells per ml (i.e. $1 \times 10^5/200$ μl/well) were stimulated in 96 well flat bottom plates with different concentrations of exemplar compounds from Table I in triplicate for a total period of 68 hours. After 68 hours, cells were pulsed with 0.75 μCi of [$^3$H]-thymidine (1Ci=37 GBq; Perkin Elmer Life Sciences) in 20 μl RPMI 1640 medium (no serum) per well and harvested 6-8 hours later. The plates were then harvested using a cell harvester and radioactive incorporation was determined using standard liquid scintillation technique. In some cases the corresponding [$^3$H]-T (cpm) was converted into a proliferation index and reported as such.

Example 5

In Vivo Cytokine Secretion in Mouse Model Treated with TLR9 Agonist Compounds

C57BL/6 mice and BALB/c mice, 5-6 weeks old, were obtained from Taconic Farms, Germantown, N.Y. and maintained in accordance with Idera Pharmaceutical's IACUC approved animal protocols. Mice (n=3) were injected subcutaneously (s.c) with individual immune modulatory compounds from Table I at 0.25 or 1.0 mg/kg (single dose). Serum was collected by retro-orbital bleeding 2 hours after immune modulatory compound administration and IL-12, IL-10, IL-6, IP-10, KC, MCP1, MIG, MIP-1α and TNF-α concentrations were determined by sandwich ELISA or Luminex multiplex assays. The results are shown in FIGS. 7A, 7B, 7C, 7D, 7E and 8F and demonstrate that in vivo administration of immune modulatory compounds containing novel chemical compositions generates unique cytokine and chemokine profiles. All reagents, including cytokine and chemokine antibodies and standards were purchased from PharMingen. (San Diego, Calif.)

EQUIVALENTS

While the foregoing invention has been described in some detail for purposes of clarity and understanding, it will be appreciated by one skilled in the art from a reading of this disclosure that various changes in form and detail can be made without departing from the true scope of the invention and appended claims.

```
SEQUENCE LISTING

<160> NUMBER OF SEQ ID NOS: 191

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 1
tcgtacgtac g                                                         11

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: AraG

<400> SEQUENCE: 2
tctgtcgttg t                                                         11

<210> SEQ ID NO 3
<211> LENGTH: 11
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: AraG

<400> SEQUENCE: 3
tcagtcgtta c                                                            11

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: AraG

<400> SEQUENCE: 4
tctgtcgtag                                                              10

<210> SEQ ID NO 5
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG

<400> SEQUENCE: 5 tcgtcgttt                                                                9

<210> SEQ ID NO 6
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG

<400> SEQUENCE: 6 tcgtcgttt                                                                9

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic
```

```
            oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 2'-O-methylribonucleotide

<400> SEQUENCE: 7
tcgaacgttc g                                                          11

<210> SEQ ID NO 8
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG

<400> SEQUENCE: 8 tcgtcgtt                                                               8

<210> SEQ ID NO 9
<211> LENGTH: 11
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: AraG
<220> FEATURE:
<221> NAME/KEY: modified_base
<222> LOCATION: (10)..(11)
<223> OTHER INFORMATION: 2'-O-methylribonucleotide

<400> SEQUENCE: 9
tctgtcgttc u                                                          11

<210> SEQ ID NO 10
<211> LENGTH: 11
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
```

```
<222> LOCATION: (6)..(6)
<223> OTHER INFORMATION: 7-deaza-dG
<220> FEATURE:
<221> NAME/KEY: modified_base
<222> LOCATION: (10)..(11)
<223> OTHER INFORMATION: 2'-O-methylribonucleotide

<400> SEQUENCE: 10
tcgtcgtttu u                                                              11

<210> SEQ ID NO 11
<211> LENGTH: 9
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG
<220> FEATURE:
<221> NAME/KEY: modified_base
<222> LOCATION: (9)..(9)
<223> OTHER INFORMATION: 2'-deoxy-U

<400> SEQUENCE: 11 tcgtcgttu                                                                  9

<210> SEQ ID NO 12
<211> LENGTH: 9
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: AraG
<220> FEATURE:
<221> NAME/KEY: modified_base
<222> LOCATION: (6)..(6)
<223> OTHER INFORMATION: AraG
<220> FEATURE:
<221> NAME/KEY: modified_base
<222> LOCATION: (9)..(9)
<223> OTHER INFORMATION: 2'-deoxy-U

<400> SEQUENCE: 12 tcgtcgttu                                                                  9

<210> SEQ ID NO 13
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 7-deaza-dG
```

```
<400> SEQUENCE: 13
tagtcgttct c                                                          11

<210> SEQ ID NO 14
<211> LENGTH: 11
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-O-methylribonucleotide
<220> FEATURE:
<221> NAME/KEY: modified_base
<222> LOCATION: (8)..(8)
<223> OTHER INFORMATION: 7-deaza-dG

<400> SEQUENCE: 14
tcutgtcgtt c                                                          11

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG

<400> SEQUENCE: 15
tcgtcgtttt t                                                          11

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG

<400> SEQUENCE: 16
tcgtcgtttt t                                                          11

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (7)..(7)
<223> OTHER INFORMATION: 7-deaza-dG

<400> SEQUENCE: 17
tctgtcgttc t                                                           11

<210> SEQ ID NO 18
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 18
tcgaacgttc g                                                           11

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 19
tcgaacgttc g                                                           11

<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 20
```

-continued tcgaacgttc g                                                11

<210> SEQ ID NO 21
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 21
tcgaacgttc g                                                11

<210> SEQ ID NO 22
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 22
tctgtcgttc t                                                11

<210> SEQ ID NO 23
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 23
cagtcgttca g                                                11

<210> SEQ ID NO 24
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 24
cagtcgttca g                                                11

<210> SEQ ID NO 25

```
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 2'-O-methylribonucleotide

<400> SEQUENCE: 25
tcgaacgttc g                                                              11

<210> SEQ ID NO 26
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG

<400> SEQUENCE: 26
tcgtcgtttt t                                                              11

<210> SEQ ID NO 27
<211> LENGTH: 9
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: AraG
<220> FEATURE:
<221> NAME/KEY: modified_base
<222> LOCATION: (6)..(6)
<223> OTHER INFORMATION: AraG
<220> FEATURE:
<221> NAME/KEY: modified_base
<222> LOCATION: (9)..(9)
<223> OTHER INFORMATION: 2'-deoxy-U

<400> SEQUENCE: 27 tcgtcgttu                                                                  9

<210> SEQ ID NO 28
<211> LENGTH: 11
<212> TYPE: DNA
<213> ORGANISM: Artificial Sequence
<220> FEATURE:
<223> OTHER INFORMATION: Description of Combined DNA/RNA molecule:
      Synthetic oligonucleotide
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (8)..(9)
<223> OTHER INFORMATION: 2'-deoxy-U
<220> FEATURE:
<221> NAME/KEY: modified_base
<222> LOCATION: (11)..(11)
<223> OTHER INFORMATION: 2'-O-methylribonucleotide

<400> SEQUENCE: 28
tcgaacguuc g                                                          11

<210> SEQ ID NO 29
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 29
tctgtcgttc t                                                          11

<210> SEQ ID NO 30
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 30
cagtcgttca g                                                          11

<210> SEQ ID NO 31
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 31
cagtcgttca g                                                          11

<210> SEQ ID NO 32
<211> LENGTH: 11
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 32
tctgtcgttc t                                                               11

<210> SEQ ID NO 33
<211> LENGTH: 11
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (8)..(9)
<223> OTHER INFORMATION: 2'-deoxy-U
<220> FEATURE:
<221> NAME/KEY: modified_base
<222> LOCATION: (11)..(11)
<223> OTHER INFORMATION: 2'-O-methylribonucleotide

<400> SEQUENCE: 33
tcgaacguuc g                                                               11

<210> SEQ ID NO 34
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 2'-O-methylribonucleotide

<400> SEQUENCE: 34
tcgaacgttc g                                                               11

<210> SEQ ID NO 35
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
```

```
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 35
tcgaacgttc g                                                            11

<210> SEQ ID NO 36
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 36
cagtcgttca g                                                            11

<210> SEQ ID NO 37
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 37
cagtcgttca g                                                            11

<210> SEQ ID NO 38
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 38
cagtcgttca g                                                            11

<210> SEQ ID NO 39
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
```

```
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 39
tcgaacgttc g                                                              11

<210> SEQ ID NO 40
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 2'-O-methylribonucleotide

<400> SEQUENCE: 40
tcgaacgttc g                                                              11

<210> SEQ ID NO 41
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 2'-O-methylribonucleotide

<400> SEQUENCE: 41
tcgaacgttc g                                                              11

<210> SEQ ID NO 42
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 2'-O-methylribonucleotide
```

```
<400> SEQUENCE: 42
tcgaacgttc g                                                           11

<210> SEQ ID NO 43
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 43
cagtcgttca g                                                           11

<210> SEQ ID NO 44
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 2'-O-methylribonucleotide

<400> SEQUENCE: 44
tcgaacgttc g                                                           11

<210> SEQ ID NO 45
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 45
tcgaacgttc g                                                           11

<210> SEQ ID NO 46
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (7)..(7)
<223> OTHER INFORMATION: 7-deaza-dG

<400> SEQUENCE: 46
tcagtcgtta c                                                          11

<210> SEQ ID NO 47
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 47
tctgtcgttt t                                                          11

<210> SEQ ID NO 48
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 48
tcagtcgtta c                                                          11

<210> SEQ ID NO 49
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 49
tctgtcgttt t                                                          11

<210> SEQ ID NO 50
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG

<400> SEQUENCE: 50 tcgtcgtt                                                               8
```

<210> SEQ ID NO 51
<211> LENGTH: 9
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG
<220> FEATURE:
<221> NAME/KEY: modified_base
<222> LOCATION: (9)..(9)
<223> OTHER INFORMATION: 2'-deoxy-U

<400> SEQUENCE: 51 tcgtcgttu                                                              9

<210> SEQ ID NO 52
<211> LENGTH: 9
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG
<220> FEATURE:
<221> NAME/KEY: modified_base
<222> LOCATION: (9)..(9)
<223> OTHER INFORMATION: 2'-deoxy-U

<400> SEQUENCE: 52 tcgtcgttu                                                              9

<210> SEQ ID NO 53
<211> LENGTH: 9
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG
<220> FEATURE:
<221> NAME/KEY: modified_base
<222> LOCATION: (9)..(9)
<223> OTHER INFORMATION: 2'-deoxy-U

```
<400> SEQUENCE: 53 tcgtcgttu                                                                9

<210> SEQ ID NO 54
<211> LENGTH: 9
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG
<220> FEATURE:
<221> NAME/KEY: modified_base
<222> LOCATION: (9)..(9)
<223> OTHER INFORMATION: 2'-deoxy-U

<400> SEQUENCE: 54 tcgtcgttu                                                                9

<210> SEQ ID NO 55
<211> LENGTH: 9
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: AraG
<220> FEATURE:
<221> NAME/KEY: modified_base
<222> LOCATION: (6)..(6)
<223> OTHER INFORMATION: AraG
<220> FEATURE:
<221> NAME/KEY: modified_base
<222> LOCATION: (9)..(9)
<223> OTHER INFORMATION: 2'-deoxy-U

<400> SEQUENCE: 55 tcgtcgttu                                                                9

<210> SEQ ID NO 56
<211> LENGTH: 9
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: AraG
<220> FEATURE:
<221> NAME/KEY: modified_base
<222> LOCATION: (6)..(6)
<223> OTHER INFORMATION: AraG
```

```
<220> FEATURE:
<221> NAME/KEY: modified_base
<222> LOCATION: (9)..(9)
<223> OTHER INFORMATION: 2'-deoxy-U

<400> SEQUENCE: 56 tcgtcgttu                                                                  9

<210> SEQ ID NO 57
<211> LENGTH: 9
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: AraG
<220> FEATURE:
<221> NAME/KEY: modified_base
<222> LOCATION: (6)..(6)
<223> OTHER INFORMATION: AraG
<220> FEATURE:
<221> NAME/KEY: modified_base
<222> LOCATION: (9)..(9)
<223> OTHER INFORMATION: 2'-deoxy-U

<400> SEQUENCE: 57 tcgtcgttu                                                                  9

<210> SEQ ID NO 58
<211> LENGTH: 9
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: AraG
<220> FEATURE:
<221> NAME/KEY: modified_base
<222> LOCATION: (6)..(6)
<223> OTHER INFORMATION: AraG
<220> FEATURE:
<221> NAME/KEY: modified_base
<222> LOCATION: (9)..(9)
<223> OTHER INFORMATION: 2'-deoxy-U

<400> SEQUENCE: 58 tcgtcgttu                                                                  9

<210> SEQ ID NO 59
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
```

```
<223> OTHER INFORMATION: 7-deaza-dG
<220> FEATURE:
<221> NAME/KEY: modified_base
<222> LOCATION: (9)..(9)
<223> OTHER INFORMATION: 7-deaza-dG

<400> SEQUENCE: 59
tcgtcgacga t                                                         11

<210> SEQ ID NO 60
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: AraG

<400> SEQUENCE: 60
tcagtcgtta c                                                         11

<210> SEQ ID NO 61
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 61
tcgatcgatc g                                                         11

<210> SEQ ID NO 62
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 62
tcgaacgttc g                                                         11

<210> SEQ ID NO 63
<211> LENGTH: 11
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 2'-O-methylribonucleotide

<400> SEQUENCE: 63
tcgaacgttc g                                                          11

<210> SEQ ID NO 64
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 64
tcgaacgttc g                                                          11

<210> SEQ ID NO 65
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 7-deaza-dG

<400> SEQUENCE: 65
tagtcgtttt t                                                          11

<210> SEQ ID NO 66
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tcgtcgttct t                                                          11

<210> SEQ ID NO 67
<211> LENGTH: 11
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 67
tggtcgttct t                                                           11

<210> SEQ ID NO 68
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 68
tagtcgttct c                                                           11

<210> SEQ ID NO 69
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG

<400> SEQUENCE: 69
tcgtcgtttt t                                                           11

<210> SEQ ID NO 70
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG

<400> SEQUENCE: 70
tcgtcgtttt t                                                           11

<210> SEQ ID NO 71
<211> LENGTH: 11
<212> TYPE: DNA
<213> ORGANISM: Artificial Sequence
<220> FEATURE:
<223> OTHER INFORMATION: Description of Artificial Sequence: Synthetic
```

```
            oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG

<400> SEQUENCE: 71
tcgtcgtttt t                                                               11

<210> SEQ ID NO 72
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 7-deaza-dG

<400> SEQUENCE: 72
tcttgtcgtt c                                                               11

<210> SEQ ID NO 73
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 7-deaza-dG

<400> SEQUENCE: 73
tcttgtcgtt c                                                               11

<210> SEQ ID NO 74
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-araG

<400> SEQUENCE: 74
tctgtcgttc t                                                               11

<210> SEQ ID NO 75
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-araG
<220> FEATURE:
<221> NAME/KEY: modified_base
<222> LOCATION: (7)..(7)
```

```
<223> OTHER INFORMATION: 7-deaza-araG
<220> FEATURE:
<221> NAME/KEY: modified_base
<222> LOCATION: (11)..(11)
<223> OTHER INFORMATION: 7-deaza-araG

<400> SEQUENCE: 75
tcgaacgttc g                                                              11

<210> SEQ ID NO 76
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG

<400> SEQUENCE: 76
tcgtcgtttt t                                                              11

<210> SEQ ID NO 77
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG

<400> SEQUENCE: 77
tcgtcgtttt t                                                              11

<210> SEQ ID NO 78
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG

<400> SEQUENCE: 78
tcgtcgtttt t                                                              11

<210> SEQ ID NO 79
<211> LENGTH: 11
<212> TYPE: DNA
<213> ORGANISM: Artificial Sequence
<220> FEATURE:
<223> OTHER INFORMATION: Description of Artificial Sequence: Synthetic
```

```
         oligonucleotide
<220> FEATURE:
<221> NAME/KEY: modified_base
<222> LOCATION: (7)..(7)
<223> OTHER INFORMATION: 7-deaza-dG

<400> SEQUENCE: 79
tctgtcgttc t                                                              11

<210> SEQ ID NO 80
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 80
tcgaacgttc g                                                              11

<210> SEQ ID NO 81
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 81
cagtcgttca g                                                              11

<210> SEQ ID NO 82
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 82
cagtcgttca g                                                              11

<210> SEQ ID NO 83
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
```

<223> OTHER INFORMATION: AraG

<400> SEQUENCE: 83
cagtcgttca g                                                          11

<210> SEQ ID NO 84
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 84
cagtcgttca g                                                          11

<210> SEQ ID NO 85
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 85
cagtcgttca g                                                          11

<210> SEQ ID NO 86
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 86
cagtcgttca g                                                          11

<210> SEQ ID NO 87
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 87
cagtcgttca g                                                          11

<210> SEQ ID NO 88
<211> LENGTH: 11
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 88
cagtcgttca g                                                              11

<210> SEQ ID NO 89
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 89
tcgaacgttc g                                                              11

<210> SEQ ID NO 90
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 90
tcgaacgttc g                                                              11

<210> SEQ ID NO 91
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
```

-continued

```
<223> OTHER INFORMATION: 2'-O-methylribonucleotide

<400> SEQUENCE: 91
tcgaacgttc g                                                            11

<210> SEQ ID NO 92
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 92
tcgaacgttc g                                                            11

<210> SEQ ID NO 93
<211> LENGTH: 11
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (8)..(9)
<223> OTHER INFORMATION: 2'-deoxy-U
<220> FEATURE:
<221> NAME/KEY: modified_base
<222> LOCATION: (11)..(11)
<223> OTHER INFORMATION: 7-deaza-dG

<400> SEQUENCE: 93
tcgaacguuc g                                                            11

<210> SEQ ID NO 94
<211> LENGTH: 11
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
```

```
<222> LOCATION: (7)..(7)
<223> OTHER INFORMATION: 7-deaza-dG
<220> FEATURE:
<221> NAME/KEY: modified_base
<222> LOCATION: (8)..(9)
<223> OTHER INFORMATION: 2'-deoxy-U
<220> FEATURE:
<221> NAME/KEY: modified_base
<222> LOCATION: (11)..(11)
<223> OTHER INFORMATION: 2'-O-methylribonucleotide

<400> SEQUENCE: 94
tcgaacguuc g                                                         11

<210> SEQ ID NO 95
<211> LENGTH: 11
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (8)..(9)
<223> OTHER INFORMATION: 2'-deoxy-U
<220> FEATURE:
<221> NAME/KEY: modified_base
<222> LOCATION: (11)..(11)
<223> OTHER INFORMATION: 2'-O-methylribonucleotide

<400> SEQUENCE: 95
tcgaacguuc g                                                         11

<210> SEQ ID NO 96
<211> LENGTH: 11
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (8)..(9)
<223> OTHER INFORMATION: 2'-deoxy-U
<220> FEATURE:
<221> NAME/KEY: modified_base
<222> LOCATION: (11)..(11)
<223> OTHER INFORMATION: 2'-O-methylribonucleotide

<400> SEQUENCE: 96
tcgaacguuc g                                                         11
```

```
<210> SEQ ID NO 97
<211> LENGTH: 11
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (8)..(9)
<223> OTHER INFORMATION: 2'-deoxy-U
<220> FEATURE:
<221> NAME/KEY: modified_base
<222> LOCATION: (11)..(11)
<223> OTHER INFORMATION: 2'-O-methylribonucleotide

<400> SEQUENCE: 97
tcgaacguuc g                                                           11

<210> SEQ ID NO 98
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 98
tcgaacgttc g                                                           11

<210> SEQ ID NO 99
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG

<400> SEQUENCE: 99
tcgtcgttct                                                             10

<210> SEQ ID NO 100
<211> LENGTH: 11
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 100
tctgtcgttc g                                                          11

<210> SEQ ID NO 101
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 101
tcggtcgttc g                                                          11

<210> SEQ ID NO 102
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 102
tctgtcgttc t                                                          11

<210> SEQ ID NO 103
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 103
tctgtcgttc t                                                          11
```

```
<210> SEQ ID NO 104
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 104
tctgtcgttc t                                                              11

<210> SEQ ID NO 105
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 105
tctgtcgttc t                                                              11

<210> SEQ ID NO 106
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 7-deaza-araG

<400> SEQUENCE: 106
cagtcgttca g                                                              11

<210> SEQ ID NO 107
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-araG

<400> SEQUENCE: 107
tctgtcgttc t                                                              11

<210> SEQ ID NO 108
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
```

```
<223> OTHER INFORMATION: 7-deaza-dG

<400> SEQUENCE: 108
tctgtcgttc t                                                           11

<210> SEQ ID NO 109
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 109
tctgtcgttc t                                                           11

<210> SEQ ID NO 110
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 110
tctgtcgttc t                                                           11

<210> SEQ ID NO 111
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 111
tctgtcgttc t                                                           11

<210> SEQ ID NO 112
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 112
tctgtcgttc t                                                           11

<210> SEQ ID NO 113
<211> LENGTH: 11
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 113
tcgaacgttc g                                                          11

<210> SEQ ID NO 114
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 114
tcgaacgttc g                                                          11

<210> SEQ ID NO 115
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 115
tcgaacgttc g                                                          11

<210> SEQ ID NO 116
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)

```
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 116
tcgaacgttc g                                                        11

<210> SEQ ID NO 117
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 117
tcgaacgttc g                                                        11

<210> SEQ ID NO 118
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 118
cagtcgttca g                                                        11

<210> SEQ ID NO 119
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 119
cagtcgttca g                                                        11

<210> SEQ ID NO 120
<211> LENGTH: 11
<212> TYPE: DNA
<213> ORGANISM: Artificial Sequence
<220> FEATURE:
<223> OTHER INFORMATION: Description of Artificial Sequence: Synthetic
```

```
           oligonucleotide
<220> FEATURE:
<221> NAME/KEY: modified_base
<222> LOCATION: (6)..(6)
<223> OTHER INFORMATION: AraG

<400> SEQUENCE: 120
cagtcgttca g                                                              11

<210> SEQ ID NO 121
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 121
cagtcgttca g                                                              11

<210> SEQ ID NO 122
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 2'-O-methylribonucleotide

<400> SEQUENCE: 122
tcgaacgttc g                                                              11

<210> SEQ ID NO 123
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 123
tcagtcgtta c                                                              11

<210> SEQ ID NO 124
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
```

```
<223> OTHER INFORMATION: 7-deaza-dG

<400> SEQUENCE: 124
tctgtcgtta g                                                              11

<210> SEQ ID NO 125
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 125
tctgtcgttt t                                                              11

<210> SEQ ID NO 126
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 126
tctgtcgttg t                                                              11

<210> SEQ ID NO 127
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 2'-O-methylribonucleotide

<400> SEQUENCE: 127
tcgaacgttc g                                                              11

<210> SEQ ID NO 128
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
```

```
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 128
tcgaacgttc g                                                          11

<210> SEQ ID NO 129
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 129
tcgaacgttc g                                                          11

<210> SEQ ID NO 130
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 2'-O-methylribonucleotide

<400> SEQUENCE: 130
tcgaacgttc g                                                          11

<210> SEQ ID NO 131
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 2'-O-methylribonucleotide
```

<400> SEQUENCE: 131
tcgaacgttc g                                                                                          11

<210> SEQ ID NO 132
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG

<400> SEQUENCE: 132
tcgtcgtttt t                                                                                          11

<210> SEQ ID NO 133
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG

<400> SEQUENCE: 133
tcgtcgtttt t                                                                                          11

<210> SEQ ID NO 134
<211> LENGTH: 9
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: AraG
<220> FEATURE:
<221> NAME/KEY: modified_base
<222> LOCATION: (6)..(6)
<223> OTHER INFORMATION: AraG
<220> FEATURE:
<221> NAME/KEY: modified_base
<222> LOCATION: (9)..(9)
<223> OTHER INFORMATION: 2'-deoxy-U

<400> SEQUENCE: 134 tcgtcgttu                                                                                              9

<210> SEQ ID NO 135
<211> LENGTH: 11
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 135
tcgaacgttc g                                                              11

<210> SEQ ID NO 136
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 136
tctgtcgtta c                                                              11

<210> SEQ ID NO 137
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 137
tctgtcgttg t                                                              11

<210> SEQ ID NO 138
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 138
tcagtcgttc t                                                              11

<210> SEQ ID NO 139
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 139
tcgaacgttc g                                                            11

<210> SEQ ID NO 140
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 140
tcgaacgttc g                                                            11

<210> SEQ ID NO 141
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 141
tctgtcgtta c                                                            11

<210> SEQ ID NO 142
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 142
tctgtcgttg t                                                            11

<210> SEQ ID NO 143
<211> LENGTH: 11
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 143
tcagtcgtta g                                                          11

<210> SEQ ID NO 144
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 144
tcagtcgtta c                                                          11

<210> SEQ ID NO 145
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 145
tctgtcgtta g                                                          11

<210> SEQ ID NO 146
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 146
tctgtcgttt t                                                          11

<210> SEQ ID NO 147
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 147
tctgtcgttg t                                                          11
```

```
<210> SEQ ID NO 148
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 148
cagtcgttca g                                                          11

<210> SEQ ID NO 149
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 149
tcagtcgtta c                                                          11

<210> SEQ ID NO 150
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 150
tctgtcgtta g                                                          11

<210> SEQ ID NO 151
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 151
tctgtcgttt t                                                          11

<210> SEQ ID NO 152
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG
```

<400> SEQUENCE: 152
tctgtcgttg t                                                                            11

<210> SEQ ID NO 153
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 153
tcgaacgttc g                                                                            11

<210> SEQ ID NO 154
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 154
tcgaacgttc g                                                                            11

<210> SEQ ID NO 155
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 155
tcgtacgtac g                                                                            11

```
<210> SEQ ID NO 156
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 156
tcgtacgtac g                                                          11

<210> SEQ ID NO 157
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 157
tcgtacgtac g                                                          11

<210> SEQ ID NO 158
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 158
cagtcgttca g                                                          11

<210> SEQ ID NO 159
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 7-deaza-dG
```

```
<400> SEQUENCE: 159
tagtcgtttt t                                                              11

<210> SEQ ID NO 160
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 160
tctgtcgttc t                                                              11

<210> SEQ ID NO 161
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 161
tctgtcgttc t                                                              11

<210> SEQ ID NO 162
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG

<400> SEQUENCE: 162
tctgtcgttc t                                                              11

<210> SEQ ID NO 163
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 163
tcgaacgttc g                                                              11
```

-continued

```
<210> SEQ ID NO 164
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 164
tcgaacgttc g                                                           11

<210> SEQ ID NO 165
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 165
tcgaacgttc g                                                           11

<210> SEQ ID NO 166
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG

<400> SEQUENCE: 166
tcgaacgttc g                                                           11

<210> SEQ ID NO 167
<211> LENGTH: 11
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
```

-continued

```
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (8)..(9)
<223> OTHER INFORMATION: 2'-deoxy-U
<220> FEATURE:
<221> NAME/KEY: modified_base
<222> LOCATION: (11)..(11)
<223> OTHER INFORMATION: 2'-O-methylribonucleotide

<400> SEQUENCE: 167
tcgaacguuc g                                                            11

<210> SEQ ID NO 168
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 7-deaza-dG
<220> FEATURE:
<221> NAME/KEY: modified_base
<222> LOCATION: (9)..(9)
<223> OTHER INFORMATION: 7-deaza-dG

<400> SEQUENCE: 168
tcgtcgacga t                                                            11

<210> SEQ ID NO 169
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 169
tcgatcgatc g                                                            11

<210> SEQ ID NO 170
<211> LENGTH: 11
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: modified_base
<222> LOCATION: (7)..(7)
<223> OTHER INFORMATION: AraG

<400> SEQUENCE: 170
tctgtcgtta g                                                          11

<210> SEQ ID NO 171
<211> LENGTH: 11
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-O-methylribonucleotide
<220> FEATURE:
<221> NAME/KEY: modified_base
<222> LOCATION: (7)..(7)
<223> OTHER INFORMATION: 7-deaza-dG

<400> SEQUENCE: 171
tcugtcgttc t                                                          11

<210> SEQ ID NO 172
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 2'-O-methylribonucleotide
<220> FEATURE:
<221> NAME/KEY: modified_base
<222> LOCATION: (11)..(11)
<223> OTHER INFORMATION: 7-deaza-dG

<400> SEQUENCE: 172
tcgttctgtc gttct                                                      15

<210> SEQ ID NO 173
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (10)..(11)
<223> OTHER INFORMATION: 2'-O-methylribonucleotide

<400> SEQUENCE: 173
tctgtcgaca g                                                          11
```

-continued

```
<210> SEQ ID NO 174
<211> LENGTH: 11
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: 2'-O-methylribonucleotide
<220> FEATURE:
<221> NAME/KEY: modified_base
<222> LOCATION: (7)..(7)
<223> OTHER INFORMATION: 7-deaza-dG

<400> SEQUENCE: 174
tcugtcgttc t                                                             11

<210> SEQ ID NO 175
<211> LENGTH: 15
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(7)
<223> OTHER INFORMATION: 2'-O-methylribonucleotide
<220> FEATURE:
<221> NAME/KEY: modified_base
<222> LOCATION: (11)..(11)
<223> OTHER INFORMATION: 7-deaza-dG

<400> SEQUENCE: 175
tcgttcugtc gttct                                                         15

<210> SEQ ID NO 176
<211> LENGTH: 14
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (5)..(6)
<223> OTHER INFORMATION: 2'-O-methylribonucleotide
<220> FEATURE:
<221> NAME/KEY: modified_base
<222> LOCATION: (11)..(11)
<223> OTHER INFORMATION: AraG

<400> SEQUENCE: 176
tcgtucagtc gttc                                                          14
```

```
<210> SEQ ID NO 177
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (12)..(12)
<223> OTHER INFORMATION: AraG

<400> SEQUENCE: 177
tcgttcagtc gttc                                                       14

<210> SEQ ID NO 178
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 2'-O-methylribonucleotide
<220> FEATURE:
<221> NAME/KEY: modified_base
<222> LOCATION: (11)..(11)
<223> OTHER INFORMATION: 7-deaza-dG

<400> SEQUENCE: 178
tcgttctgtc gttgt                                                      15

<210> SEQ ID NO 179
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 7-deaza-dG

<400> SEQUENCE: 179
tatgcgtttt t                                                          11

<210> SEQ ID NO 180
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methylribonucleotide
<220> FEATURE:
<221> NAME/KEY: modified_base
<222> LOCATION: (7)..(7)
<223> OTHER INFORMATION: 7-deaza-dG
```

-continued

```
<400> SEQUENCE: 180
tctgtcgttc t                                                    11

<210> SEQ ID NO 181
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 2'-O-methylribonucleotide
<220> FEATURE:
<221> NAME/KEY: modified_base
<222> LOCATION: (11)..(11)
<223> OTHER INFORMATION: 7-deaza-dG

<400> SEQUENCE: 181
tccttctgtc gttct                                                15

<210> SEQ ID NO 182
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 182
cattcgttca g                                                    11

<210> SEQ ID NO 183
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: AraG

<400> SEQUENCE: 183
cattcgttca g                                                    11

<210> SEQ ID NO 184
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (7)..(7)
<223> OTHER INFORMATION: 7-deaza-dG

<400> SEQUENCE: 184
tcggtcgttc t                                                    11
```

-continued

```
<210> SEQ ID NO 185
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-deaza-dG
<220> FEATURE:
<221> NAME/KEY: modified_base
<222> LOCATION: (11)..(11)
<223> OTHER INFORMATION: 7-deaza-dG

<400> SEQUENCE: 185
tctgtcgttc g                                                          11

<210> SEQ ID NO 186
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(6)
<223> OTHER INFORMATION: 2'-O-methylribonucleotide
<220> FEATURE:
<221> NAME/KEY: modified_base
<222> LOCATION: (11)..(11)
<223> OTHER INFORMATION: AraG

<400> SEQUENCE: 186
tcgttcagtc gttc                                                       14

<210> SEQ ID NO 187
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (11)..(11)
<223> OTHER INFORMATION: AraG

<400> SEQUENCE: 187
tcgttcagtc gttc                                                       14

<210> SEQ ID NO 188
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
```

```
<221> NAME/KEY: modified_base
<222> LOCATION: (6)..(6)
<223> OTHER INFORMATION: 2'-O-methylribonucleotide
<220> FEATURE:
<221> NAME/KEY: modified_base
<222> LOCATION: (11)..(11)
<223> OTHER INFORMATION: 7-deaza-dG

<400> SEQUENCE: 188
tcgttctgtc gttac                                                        15

<210> SEQ ID NO 189
<211> LENGTH: 15
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(7)
<223> OTHER INFORMATION: 2'-O-methylribonucleotide
<220> FEATURE:
<221> NAME/KEY: modified_base
<222> LOCATION: (11)..(11)
<223> OTHER INFORMATION: 7-deaza-dG

<400> SEQUENCE: 189
tcgttcugtc gttgt                                                        15

<210> SEQ ID NO 190
<211> LENGTH: 15
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(7)
<223> OTHER INFORMATION: 2'-O-methylribonucleotide
<220> FEATURE:
<221> NAME/KEY: modified_base
<222> LOCATION: (11)..(11)
<223> OTHER INFORMATION: 7-deaza-dG

<400> SEQUENCE: 190
tcgttcugtc gttga                                                        15

<210> SEQ ID NO 191
<211> LENGTH: 15
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (3)..(3)
<223> OTHER INFORMATION: 7-deaza-dG
<220> FEATURE:
<221> NAME/KEY: modified_base
<222> LOCATION: (6)..(7)
<223> OTHER INFORMATION: 2'-O-methylribonucleotide
<220> FEATURE:
<221> NAME/KEY: modified_base
<222> LOCATION: (11)..(11)
<223> OTHER INFORMATION: 7-deaza-dG

<400> SEQUENCE: 191
tcgttcugtc gttac                                                         15
```

What is claimed:

1. An immune modulatory compound selected from the group consisting of 5'-TCG$_1$TACG$_1$TACG$_1$-X-G$_1$CATG$_1$CATG$_1$CT-5' [SEQ ID NO.:1], 5'-CAGTCoG$_2$TTCAG-X-GACTTG$_2$CoTTAC-5' [SEQ ID NO.:85], 5'-TCG$_1$AACG$_1$TTCG$_1$-L$_2$-G$_1$CTTG$_1$CAAG$_1$CT-5' [SEQ ID NO.:98], 5'-TCG$_1$AACG$_1$TTCG$_1$-Z-G$_1$CTTG$_1$CAAG$_1$CT-5' [SEQ ID NO.:113], 5'-TCG$_1$AACG$_1$TTCG$_1$-M-G$_1$CTTG$_1$CAAG$_1$CT-5' [SEQ ID NO.:114], 5'-TCG$_1$AACG$_1$TTCG$_1$-m-G$_1$CTTG$_1$CAAG$_1$CT-5' [SEQ ID NO.:115], 5'-TCG$_1$AACG$_1$TTCG$_1$-X$_2$-G$_1$CTTG$_1$CAAG$_1$CT-5' [SEQ ID NO.:116], 5'-TCG$_1$AACG$_1$TTCG$_1$-X$_1$-G$_1$CTTG$_1$CAAG$_1$CT-5' [SEQ ID NO.:117], and 5'-TCG$_1$AACG$_1$oTTCG$_1$-Z-G$_1$CTToG$_1$CAAG$_1$CT-5' [SEQ ID NO.:153], wherein G$_1$=7-deaza-dG; G$_2$=AraG; o=phosphodiester linkage; L$_2$=tetraethylene glycol linker; M=cis,cis-1,3,5-cyclohexanetriol linker; m=cis,trans-1,3,5-cyclohexanetriol linker; X=glycerol linker; X$_1$=1,2,4-butanetriol linker; X$_2$=1,3,5-tris(2-hydroxyethyl)cyanuric acid linker; and Z=1,3,5-pentanetriol linker.

2. A composition comprising the immune modulatory compound of claim 1 and a physiologically acceptable carrier.

3. A method for generating an immune response in an individual, the method comprising administering to the individual a compound according to claim 1 in a pharmaceutically effective amount.

4. A method for therapeutically treating an individual having a disease or disorder where modulating an immune response would be beneficial, such method comprising administering to the individual a compound according to claim 1 in a pharmaceutically effective amount.

5. The method of claim 4, wherein the disease or disorder is cancer, an autoimmune disorder, airway inflammation, inflammatory disorder, infectious disease, skin disorder, allergy, asthma or a disease caused by a pathogen or allergen.

6. The method according to claim 4, further comprising administering one or more chemotherapeutic compounds, targeted therapeutic agents, vaccines, antigens, antibodies, cytotoxic agents, allergens, antibiotics, antisense oligonucleotides, TLR agonists, kinase inhibitors, peptides, proteins, DNA vaccines, adjuvants, co-stimulatory molecules or combinations thereof.

* * * * *

UNITED STATES PATENT AND TRADEMARK OFFICE
CERTIFICATE OF CORRECTION

PATENT NO.      : 7,960,362 B2                                      Page 1 of 3
APPLICATION NO. : 12/183439
DATED           : June 14, 2011
INVENTOR(S)     : Kandimalla et al.

It is certified that error appears in the above-identified patent and that said Letters Patent is hereby corrected as shown below:

At Col. 10, in Table 1, replace the following lines:

| | |
|---|---|
| 17 (17) | 5'-TCTGTCG$_1$TTCT-Y-TCTTG$_1$CTGYYTTG$_1$CT-5' |
| 18 (18 & 172) | 5'-TCG$_1$AACG$_1$TTCG$_1$-Y-TCTTG$_1$CTGT<u>C</u>TTG$_1$CT-5' |
| 19 (19) | 5'-TCG$_1$AACG$_1$TTCG$_1$-Y-TCTTG$_1$CTG<u>LL</u>TTG$_1$CT-5' | with:

| | |
|---|---|
| 17 (17 & 192) | 5'-TCTGTCG$_1$TTCT-Y-TCTTG$_1$CTGYYTTG$_1$CT-5' |
| 18 (18 & 172) | 5'-TCG$_1$AACG$_1$TTCG$_1$-Y-TCTTG$_1$CTGT<u>C</u>TTG$_1$CT-5' |
| 19 (19 & 193) | 5'-TCG$_1$AACG$_1$TTCG$_1$-Y-TCTTG$_1$CTG<u>LL</u>TTG$_1$CT-5' |

At Col. 13, in Table 1, replace the following lines:

| | |
|---|---|
| 77 (77) | 5'-TCG$_1$TCG$_1$TTTTT-X-TCTTG$_1$CTGYYTTG$_1$CT-5' |
| 78 (78) | 5'-TCG$_1$TCG$_1$TTTTT-X-TCTTG$_1$CTG<u>LL</u>TTG$_1$CT-5' |
| 79 (79) | 5'-TCTGTCG$_1$TTCT-Y-TCTTG$_1$CTG<u>LL</u>TTG$_1$CT-5' | with:

| | |
|---|---|
| 77 (77 & 192) | 5'-TCG$_1$TCG$_1$TTTTT-X-TCTTG$_1$CTGYYTTG$_1$CT-5' |
| 78 (78 & 193) | 5'-TCG$_1$TCG$_1$TTTTT-X-TCTTG$_1$CTG<u>LL</u>TTG$_1$CT-5' |
| 79 (79 & 193) | 5'-TCTGTCG$_1$TTCT-Y-TCTTG$_1$CTG<u>LL</u>TTG$_1$CT-5' |

At Col. 15, in Table 1, replace the following lines:

| | |
|---|---|
| 136 (136) | 5'-TCTGTCG$_1$TTAC-Y$_3$-CATTG$_1$CTGYYTTG$_1$CT-5' |
| 137 (137) | 5'-TCTGTCG$_1$TTGT-Y$_3$-TGTTG$_1$CTGYYTTG$_1$CT-5' |
| 138 (138) | 5'-TCAGTCG$_1$TTCT-Y$_3$-CATTG$_1$CTGYYTTG$_1$CT-5' | with:

Signed and Sealed this
Seventeenth Day of April, 2012

David J. Kappos
*Director of the United States Patent and Trademark Office*

136 (136 & 194)        5'-TCTGTCG$_1$TTAC-Y$_3$-CATTG$_1$CTGYYTTG$_1$CT-5'

137 (137 & 195)        5'-TCTGTCG$_1$TTGT-Y$_3$-TGTTG$_1$CTGYYTTG$_1$CT-5'

138 (138 & 194)        5'-TCAGTCG$_1$TTCT-Y$_3$-CATTG$_1$CTGYYTTG$_1$CT-5'

In the sequence listing, at line <160>, replace:

" <160> 191 "

with:

-- <160> 195 --

In the sequence listing, add the following lines at the end of the listing:

```
<210>   192
<211>   15
<212>   DNA
<213>   Artificial Sequence

<220>
<223>   Synthetic oligonucleotide

<220>
<221>   modified_base
<222>   (3)..(3)
<223>   7-deaza-dG

<220>
<221>   misc_feature
<222>   (6)..(7)
<223>   1,3-propanediol

<220>
<221>   modified_base
<222>   (11)..(11)
<223>   7-deaza-dG

<400>   192
tcgttnngtc gttct                                                        15

<210>   193
<211>   15
<212>   DNA
<213>   Artificial Sequence

<220>
<223>   Synthetic oligonucleotide

<220>
<221>   modified_base
<222>   (3)..(3)
<223>   7-deaza-dG

<220>
<221>   misc_feature
<222>   (6)..(7)
<223>   1,2-dideoxyribose
```

```
<220>
<221>  modified_base
<222>  (11)..(11)
<223>  7-deaza-dG

<400>  193
tcgttnngtc gttct                                                         15

<210>  194
<211>  15
<212>  DNA
<213>  Artificial Sequence

<220>
<223>  Synthetic oligonucleotide

<220>
<221>  modified_base
<222>  (3)..(3)
<223>  7-deaza-dG

<220>
<221>  misc_feature
<222>  (6)..(7)
<223>  1,3-propanediol

<220>
<221>  modified_base
<222>  (11)..(11)
<223>  7-deaza-dG

<400>  194
tcgttnngtc gttac                                                         15

<210>  195
<211>  15
<212>  DNA
<213>  Artificial Sequence

<220>
<223>  Synthetic oligonucleotide

<220>
<221>  modified_base
<222>  (3)..(3)
<223>  7-deaza-dG

<220>
<221>  misc_feature
<222>  (6)..(7)
<223>  1,3-propanediol

<220>
<221>  modified_base
<222>  (11)..(11)
<223>  7-deaza-dG

<400>  195
tcgttnngtc gttgt                                                         15
```